United States Patent
Kanda et al.

(10) Patent No.: US 10,402,973 B2
(45) Date of Patent: Sep. 3, 2019

(54) IMAGE PROCESSING APPARATUS, IMAGE PROCESSING METHOD, AND COMPUTER-READABLE RECORDING MEDIUM

(71) Applicant: OLYMPUS CORPORATION, Tokyo (JP)

(72) Inventors: Yamato Kanda, Hino (JP); Takashi Kono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/790,112

(22) Filed: Oct. 23, 2017

(65) Prior Publication Data
US 2018/0047163 A1    Feb. 15, 2018

Related U.S. Application Data

(63) Continuation of application No. PCT/JP2015/062427, filed on Apr. 23, 2015.

(51) Int. Cl.
| | | |
|---|---|---|
| *G06T 7/00* | (2017.01) | |
| *A61B 1/04* | (2006.01) | |
| *G06T 7/11* | (2017.01) | |
| *G06T 7/246* | (2017.01) | |

(Continued)

(52) U.S. Cl.
CPC ............. *G06T 7/0012* (2013.01); *A61B 1/04* (2013.01); *G06T 7/11* (2017.01); *G06T 7/13* (2017.01); *G06T 7/246* (2017.01); *G06T 7/40* (2013.01); *G06T 2207/10024* (2013.01); *G06T 2207/10068* (2013.01); *G06T 2207/20076* (2013.01);

(Continued)

(58) Field of Classification Search
CPC ......... G06T 7/0012; G06T 7/11; G06T 7/246; G06T 7/13; G06T 7/40; G06T 2207/30096; G06T 2207/10068; G06T 2207/20081; A61B 1/04
USPC ........................................................ 382/128
See application file for complete search history.

(56) References Cited

U.S. PATENT DOCUMENTS

| | | |
|---|---|---|
| 8,244,009 B2 | 8/2012 | Tanaka et al. |
| 9,672,610 B2 | 6/2017 | Kanda et al. |
| 2012/0076419 A1 | 3/2012 | Kono et al. |

(Continued)

FOREIGN PATENT DOCUMENTS

| | | |
|---|---|---|
| CN | 102436650 A | 5/2012 |
| JP | 2007244519 A | 9/2007 |

(Continued)

OTHER PUBLICATIONS

International Search Report dated Jul. 14, 2015 issued in PCT/JP2015/062427.

(Continued)

*Primary Examiner* — Amandeep Saini
(74) *Attorney, Agent, or Firm* — Scully, Scott, Murphy & Presser, P.C.

(57) ABSTRACT

An image processing apparatus includes: a luminal shooting situation analysis unit configured to analyze a luminal shooting situation determined based on a relationship between a subject and an imaging unit that shoots the subject in a luminal image obtained by shooting an inside of a lumen; and a specific region detection unit configured to detect a specific region in accordance with the luminal shooting situation.

17 Claims, 26 Drawing Sheets

(51) Int. Cl.
    *G06T 7/13*    (2017.01)
    *G06T 7/40*    (2017.01)
(52) U.S. Cl.
    CPC ............... *G06T 2207/20081* (2013.01); *G06T 2207/30096* (2013.01)

(56) References Cited

U.S. PATENT DOCUMENTS

| | | | |
|---|---|---|---|
| 2013/0028485 A1 | 1/2013 | Kitamura et al. | |
| 2015/0003742 A1* | 1/2015 | Tani | G06K 9/00214 |
| | | | 382/203 |
| 2016/0014328 A1 | 1/2016 | Rokutanda | |

FOREIGN PATENT DOCUMENTS

| | | |
|---|---|---|
| JP | 2012073953 A | 4/2012 |
| JP | 2013027636 A | 2/2013 |
| JP | 2014104293 A | 6/2014 |
| JP | 2014188223 A | 10/2014 |
| JP | 2015008782 A | 1/2015 |

OTHER PUBLICATIONS

Chinese Office Action dated Oct. 29, 2018 in Chinese Patent Application No. 201580078973.X.

* cited by examiner

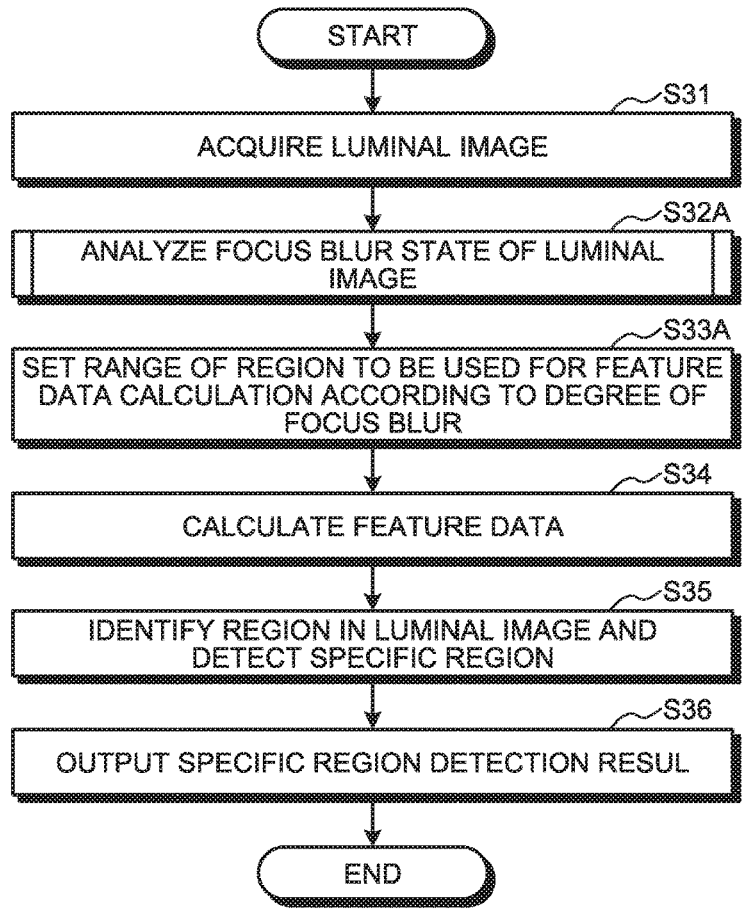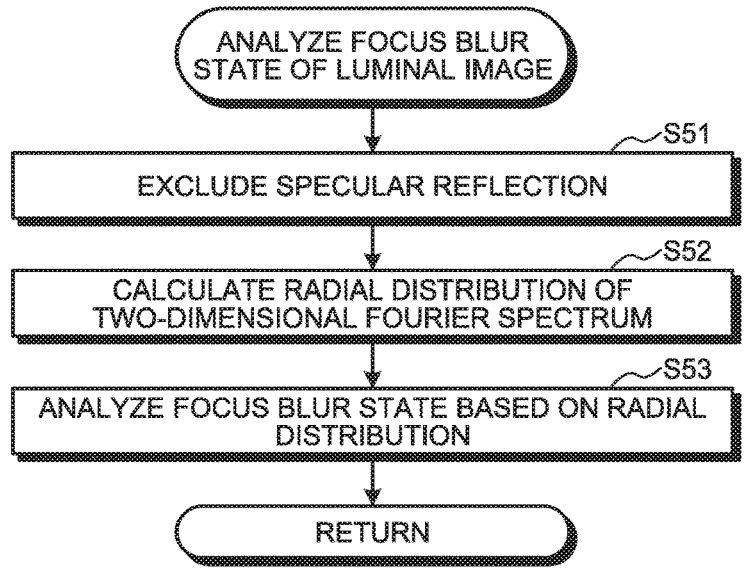

IMAGE PROCESSING APPARATUS, IMAGE PROCESSING METHOD, AND COMPUTER-READABLE RECORDING MEDIUM

CROSS-REFERENCE TO RELATED APPLICATION

This application is a continuation of International Application No. PCT/JP2015/062427, filed on Apr. 23, 2015, the entire contents of which are incorporated herein by reference.

BACKGROUND

The present disclosure relates to an image processing apparatus, an image processing method, a and a computer-readable recording medium.

In the related art, a technique for detecting an abnormal region in a living body based on pixel value gradient information of an endoscopic image, that is, pixel value surface shape feature data or a technique for detecting an abnormal region based on edge information which is contour feature data of an endoscopic image is disclosed (for example, see JP 2007-244519 A). In this technique, the abnormal region is detected by evaluating isotropy of a pixel value gradient, that is, whether or not an equivalent gradient occurs in any direction around the periphery or by evaluating whether or not an edge shape is an arc shape in a predetermined size.

SUMMARY

An image processing apparatus may include: a luminal shooting situation analysis unit configured to analyze a luminal shooting situation determined based on a relationship between a subject and an imaging unit that shoots the subject in a luminal image obtained by shooting an inside of a lumen; and a specific region detection unit configured to detect a specific region in accordance with the luminal shooting situation.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 18 is a flowchart illustrating an overview of a process performed by the image processing apparatus according to Modification 2-1 of the second embodiment;

FIG. 19 is a flowchart illustrating an overview of a process performed by a focus blur analysis unit of the image processing apparatus according to Modification 2-1 of the second embodiment;

DETAILED DESCRIPTION

Hereinafter, modes for carrying out the present disclosure (hereinafter, referred to as "embodiment(s)") will be described with reference to the appended drawings.

Figure 1:
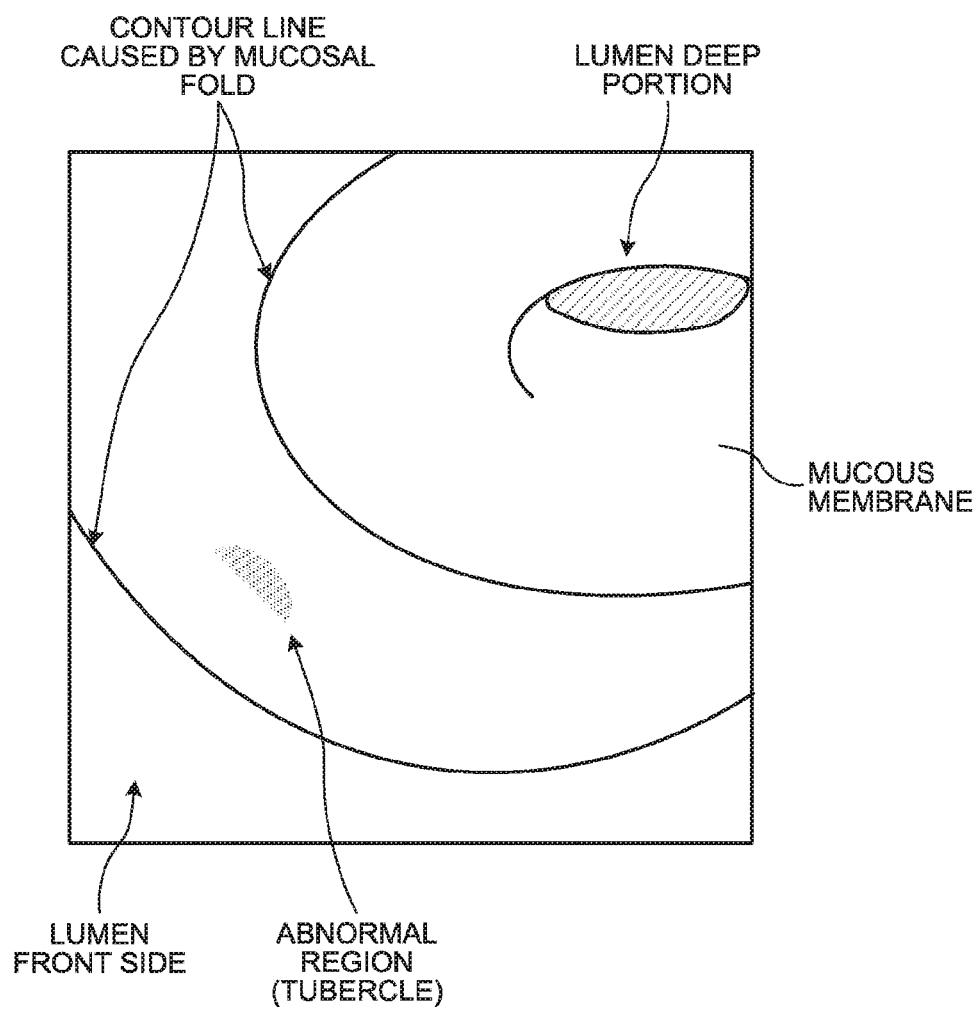
FIG. 1 is a view (Part 1) for describing an overview of an embodiment.
Figure 2:
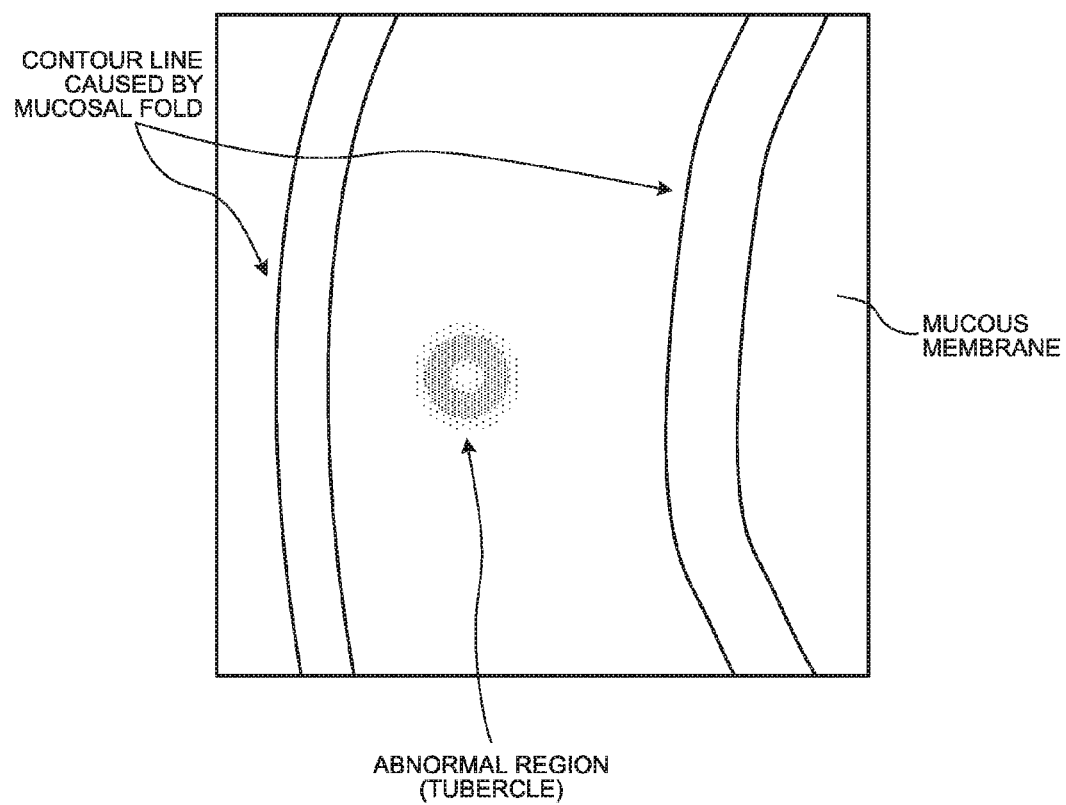
FIG. 2 is a view (Part 2) for describing the overview of the embodiment.

FIGS. 1 and 2 are views for describing an overview of an embodiment. Specifically, FIGS. 1 and 2 are views schematically illustrating images (luminal images) of a living body shot by an endoscope which is introduced into the living body and observes the living body.

The endoscope obliquely shoots a mucosal surface of a luminal wall of a living body in many cases. In this case, a portion from a mucosal surface on a lumen front side where the shooting distance is close to a mucosal surface in a lumen deep portion where the shooting distance is distant is reflected, and an abnormal region where a lesion is likely to occur is sometimes reflected in the luminal image shot by the endoscope as illustrated in FIG. 1.

On the other hand, there is also a case where the endoscope shoots the mucosal surface of the luminal wall of the living body from the front as illustrated in FIG. 2. When the mucosal surface is shot from the front, the lumen deep portion is not shot, and the way of reflecting the abnormal region is also different from that of the case of obliquely shooting the mucosal surface.

Besides, a focus blur and a motion blur occur in the image in some cases among the images shot by the endoscope since the shooting distance to the mucosal surface of the luminal wall of the living body varies according to the image.

The image processing apparatus according to the present embodiment is characterized in that adaptive detection of a specific region including the abnormal region is performed by analyzing above-described difference of a shooting situation. Here, the specific region is a region where a characteristic or a state of a subject in the luminal image satisfies a predetermined condition. For example, when the luminal image is the luminal image of the living body (intraluminal image), the specific region is a region where a tissue characteristic of the living body or the state in the living body satisfies a predetermined condition. More specifically, examples of the specific region may include the abnormal region such as a region where the tissue characteristic of the living body such as an aphtha, an ulcer, an erosion, a polyp, a tumor, redness, and villus abnormality is changed, a region where a state change in the living body, such as bleeding, occurs, and the like. The specific region may be a partial region of the image or the entire region of the image. Incidentally, a color image having pixel values for respective wavelength components of R (red), G (green), and B (blue) at each pixel position is assumed for the image shot by the endoscope, but the disclosure is limited thereto.

First Embodiment

Figure 3:
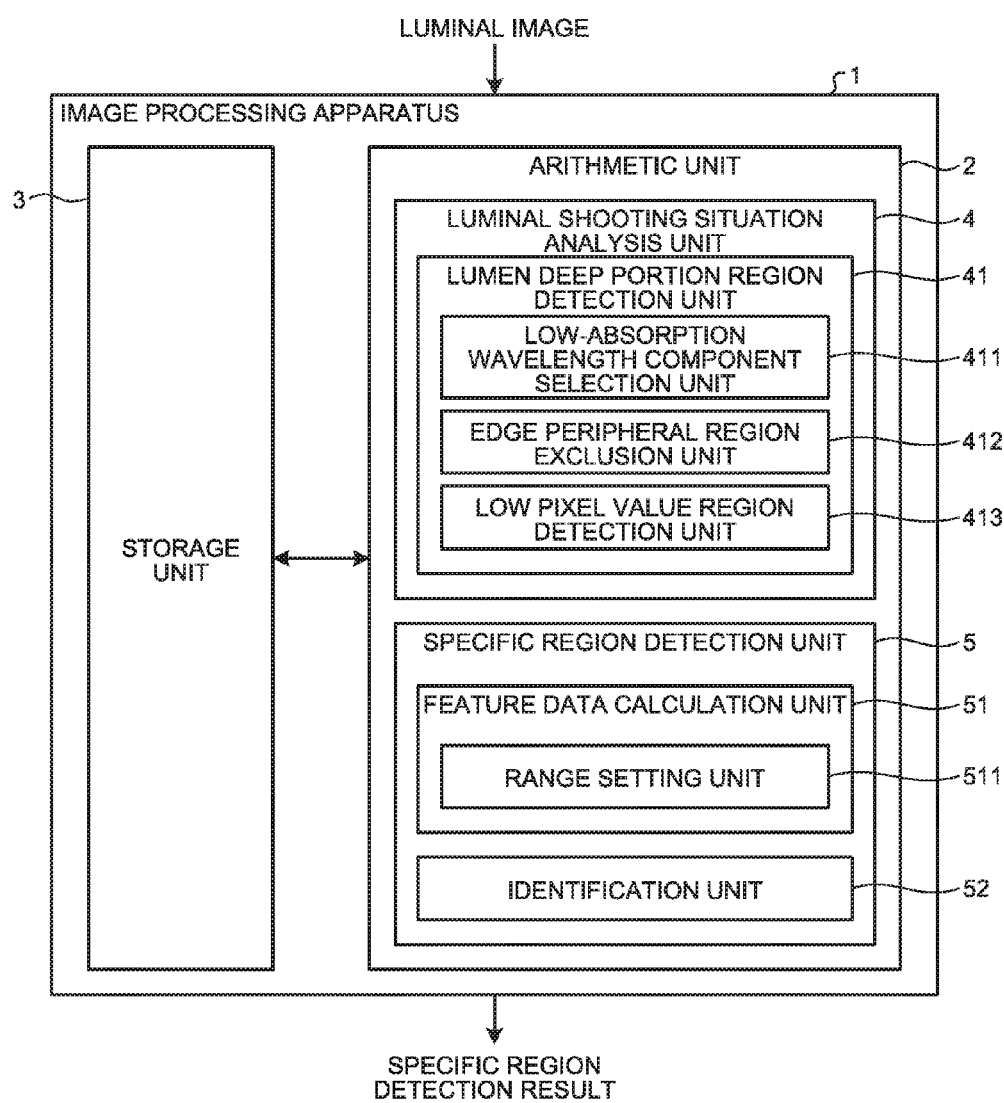
FIG. 3 is a block diagram illustrating a functional configuration of an image processing apparatus according to a first embodiment.

FIG. 3 is a block diagram illustrating a functional configuration of an image processing apparatus according to a first embodiment. An image processing apparatus 1 illustrated in this drawing includes an arithmetic unit 2 and a storage unit 3.

The arithmetic unit 2 includes a luminal shooting situation analysis unit 4, which analyzes a luminal shooting situation determined based on a relationship between the subject and an imaging unit that shoots the subject in the luminal image, and a specific region detection unit 5 that detects the specific region in accordance with the luminal shooting situation.

The luminal shooting situation analysis unit 4 includes a lumen deep portion region detection unit 41 which detects a deep region of a lumen in the luminal image. The lumen deep portion region detection unit 41 includes a low-absorption wavelength component selector 411 which selects a low-absorption wavelength component having the lowest degree of absorption and dispersion in the living body, an edge peripheral region exclusion unit 412 which excludes a pixel in an edge peripheral region in the luminal image of the low-absorption wavelength component, and a low pixel value region detection unit 413 which detects a region where a pixel value is equal to or less than a predetermined threshold in the image of the low-absorption wavelength component after excluding the pixel in the edge peripheral region.

In general, a region where the pixels detected by the low pixel value region detection unit 413 collectively exist is considered as the lumen deep portion region. The lumen deep portion region detection unit 41 performs a known labeling process (reference: CG-ARTS Society: Digital Image Processing: 181P, Labeling) on the pixel detected by the low pixel value region detection unit 413, collects the connected pixels as one region, and then, detects a largest region among regions having the area equal to or larger than a predetermined threshold as the lumen deep portion region. The lumen deep portion region detection unit 41 determines that there is no lumen deep portion region if there is no region equal to or larger than the predetermined threshold.

In the case of the image composed of R, G, and B components, for example, the low-absorption wavelength component selector 411 selects the R component which is component that is apart from an absorption band of blood and has a long wavelength, that is, the component that is hardly affected by absorption and dispersion in the living body. As the low-absorption wavelength component selector 411 performs such selection, it is possible to suppress a decrease of the pixel value caused by to a blood vessel or the like reflected on the mucosal surface and to obtain pixel value information correlating with a shooting distance to the mucosal surface the most.

The edge peripheral region exclusion unit 412 specifies an edge region by applying, for example, a known edge extraction process (reference: CG-ARTS Society: Digital Image Processing: 114P, Edge Extraction: 209P, Contour Line Detection), and then, specifies and excludes a peripheral region by performing a known inflation process (reference: CG-ARTS Society: Digital Image Processing: 179P, contraction and expansion processing) on the edge region. As the edge peripheral region exclusion unit 412 excludes the edge peripheral region, it is possible to exclude a region having a risk of being erroneously detected as a mucous membrane of a lumen deep portion (a mucous membrane in which illumination light hardly reaches and a pixel value of the low-absorption wavelength component decreases) such as a shadow part occurring in the periphery of the contour edge due to mucosal folds.

The low pixel value region detection unit 413 detects a pixel whose pixel value is equal to or less than a predetermined threshold in the image of the low-absorption wavelength component after excluding the edge peripheral region.

The specific region detection unit 5 includes a feature data calculation unit 51 and an identification unit 52. Various known items such as a color, a contour (edge), a pixel value surface shape (pixel value gradient), and texture may be exemplified as the feature data calculated by the feature data calculation unit 51. A plurality of pieces of feature data calculated from one feature data calculation region are collected as a feature vector. The feature vectors corresponding to the number of feature data calculation regions that have been set are generated.

The feature data calculation unit 51 includes a range setting unit 511 that sets a range of a region used for feature data calculation to detect a predetermined specific region according to the presence or absence of a lumen deep portion region. In a case where the lumen deep portion region is present in the luminal image, this case is a situation where the luminal wall is being shot obliquely, and thus, it is possible to detect the specific region based on global information using the whole lumen structure.

Figure 4:
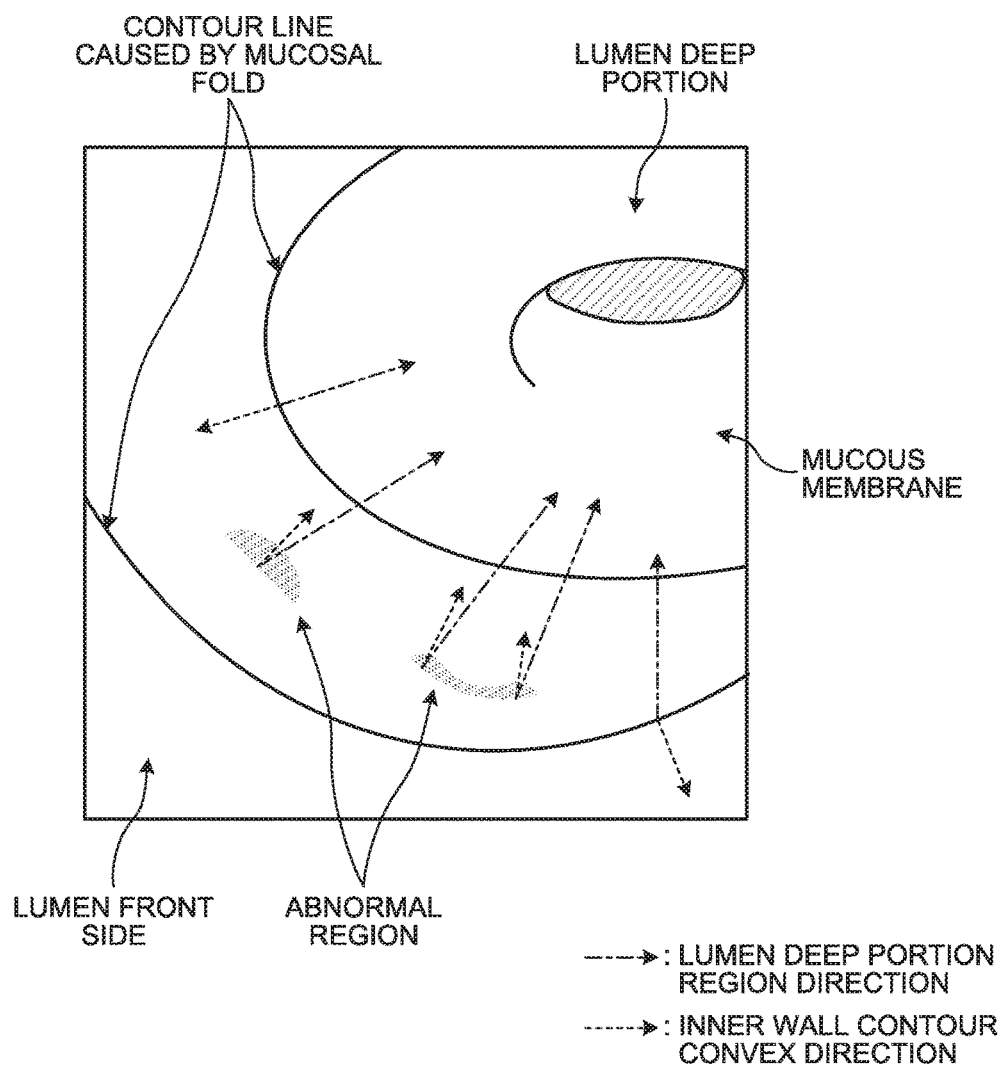
FIG. 4 is a view schematically illustrating a luminal image of a living body shot by an endoscope as an example of the luminal image.

FIG. 4 is a view schematically illustrating the luminal image of the living body shot by the endoscope as an example of the luminal image. The endoscope generally shoots the mucosal surface of the luminal wall obliquely. Thus, a portion from a mucosal surface on a lumen front side where the shooting distance is close to a mucosal surface in the lumen deep portion where the shooting distance is distant is reflected, and an abnormal region is sometimes reflected in the luminal image shot by the endoscope as illustrated in FIG. 4. A contour edge caused by the mucosal folds basically has a shape that is convex toward a side opposite to a direction of the lumen deep portion, and a shape that is convex in the lumen deep portion direction is generated in a contour edge of the abnormal region. In this manner, it is possible to perform the detection of the abnormal region based on a relationship between the lumen deep portion direction and a convex direction of an inner wall contour in the luminal image illustrated in FIG. 4.

When the lumen deep portion region is present in the luminal image, the range setting unit 511 sets the range of the region used for the feature data calculation to be relatively large so as to include the lumen deep portion region. Incidentally, even if the lumen deep portion region is not sufficiently included in the luminal image, the image processing apparatus 1 may calculate the feature data by estimating the lumen deep portion direction using a gradient of the inner wall and the like if the range of the region is large.

On the other hand, in a case where the lumen deep portion region is not present in the luminal image, this case is a situation where the luminal wall is being shot from the front, and thus, it is difficult to accurately detect the specific region based on the global information using the entire lumen structure. In this situation, if the range setting unit 511 sets the range of the region used for the feature data calculation to be large, it is likely to cause waste in the amount of operation and mixing of a region that lead to reduction in accuracy (specular reflection, residues, bubbles, normal folds, and the like). In this case, the range setting unit 511 sets the range of the region used for the feature data calculation to be smaller than that of the case where the lumen deep portion region is present in the luminal image.

The identification unit 52 identifies a region in the luminal image based on the feature vector calculated by the feature data calculation unit 51 and detects a predetermined specific region. Various identification methods based on the feature vector have been known. For example, a method of calculating an identification index P(x) on whether or not a feature vector x satisfies a specific condition based on a probability model shown in the following Formula (1) and identifying a feature data calculation region where such a value is equal to or larger than a threshold as a specific region may be exemplified as a general statistical identification method.

$$P(x) = \frac{1}{(2\pi)^{k/2} \times |Z|^{1/2}} \exp\left\{(x-\mu)^t \times \left(-\frac{1}{2}\right) Z^{-1} \times (x-\mu)\right\} \quad (1)$$

On the right side of Formula (1), k is the number of dimensions of the feature vector, x is the feature vector (k×1 matrix) of an examination region to be identified, µ is an average vector (k×1 matrix) of feature vectors of (a plurality of) samples in a specific region, Z is a variance-covariance matrix (k×k matrix) of feature vectors of (a plurality of) samples in a specific region, |Z| is a determinant of Z, and $Z^{-1}$ is an inverse matrix of Z.

Although the identification method using the probabilistic model has been exemplified herein, the identification unit 52 may also perform identification, for example, using a method based on a feature space distance from a representative feature vector, a method of setting an identification boundary in a feature space, and the like other than the above-described method.

The arithmetic unit 2 is implemented using a general-purpose processor, such as a central processing unit (CPU), or a dedicated processor such as various arithmetic circuits to execute a specific function such as an application specific integrated circuit (ASIC). When the arithmetic unit 2 is the general-purpose processor, an instruction or data is transferred to each unit constituting the image processing apparatus 1 by reading various programs stored in the storage unit 3, thereby comprehensively controlling the overall operation of the image processing apparatus 1. In addition, when the arithmetic unit 2 is the dedicated processor, the processor may execute various processes independently, or the processor and the storage unit 3 may execute various processes in cooperation or combination with each other using various types of data stored in the storage unit 3. It is a matter of course that an arithmetic unit to be described in embodiments and modifications, which will be described later, is also implemented similarly to the arithmetic unit 2.

The storage unit 3 is implemented by various IC memories such as a read only memory (ROM) and a random access memory (RAM), a hard disk that is built in or connected by a data communication terminal, or an information recording device such as a CD-ROM and a reading device thereof. The storage unit 3 stores a program configured to operate the image processing apparatus 1 and cause the image processing apparatus 1 to execute various functions, data to be used during the execution of the program, and the like in addition to image data of the luminal image acquired by the image processing apparatus 1. Specifically, the storage unit 3 stores an image processing program according to the first embodiment and various parameters such as a threshold to be used in the image processing. It is a matter of course that a storage unit to be described in the embodiments, which will be described later, is also implemented similarly to the storage unit 3.

Various programs such as the image processing program stored in the storage unit 3 may be also recorded in a computer-readable recording medium. In addition, the recording of the various programs in the storage unit 3 or the recording medium may be performed when the computer or the recording medium is shipped as a product or may be performed by download through a communication network. The communication network referred to herein is implemented, for example, using an existing public line network, local area network (LAN), wide area network (WAN), or the like, and may be implemented in an either wired or wireless manner.

The image processing apparatus 1 having the above-described configuration may be implemented using one computer or may be implemented using a plurality of computers. In the latter case, it is also possible to cause the plurality of computers to perform the processing in cooperation with each other while transmitting or receiving data via the communication network. Incidentally, the computer referred to herein may be configured by, for example, a general-purpose personal computer, a server, or the like. Regarding this point, the same description may be also applied for image processing apparatuses to be described in the embodiments and modifications which will be described later.

Incidentally, the functions of the image processing apparatus 1 described above may be provided in a processor that forms a part of an endoscope system, which is introduced into a subject and observes the inside of the subject, and controls the entire endoscope system. Regarding this point, the same description may be also applied for image processing apparatuses to be described in the embodiments and modifications which will be described later.

Figure 5:
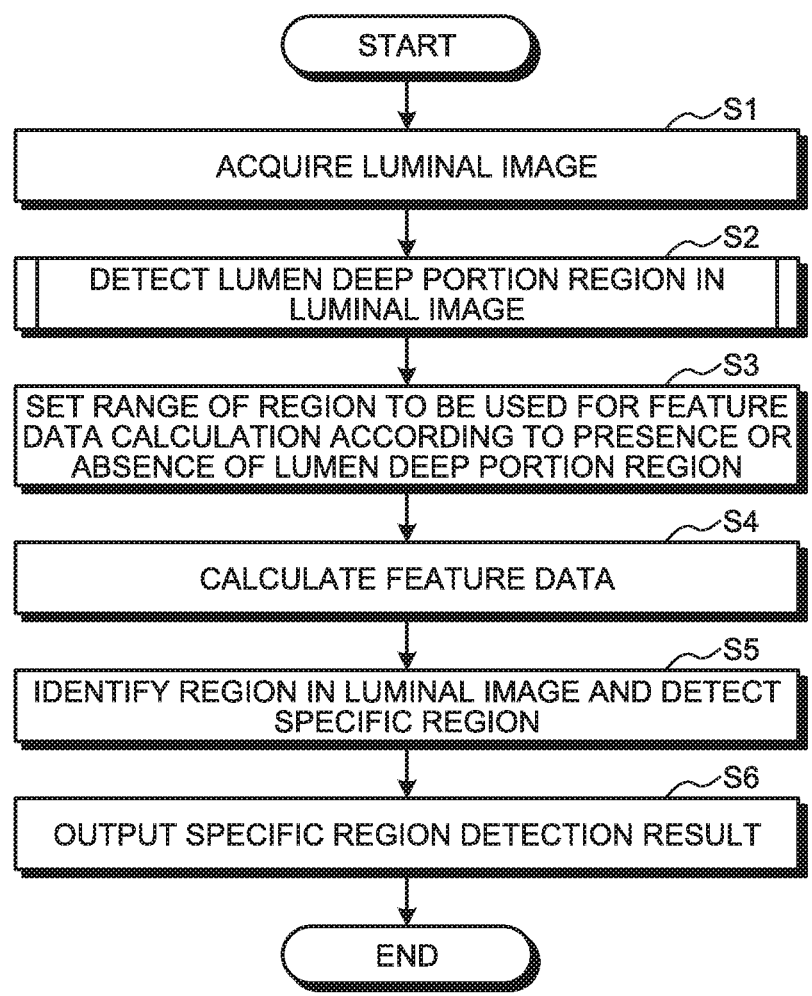
FIG. 5 is a flowchart illustrating an overview of a process performed by the image processing apparatus according to the first embodiment.

FIG. 5 is a flowchart illustrating an overview of a process executed by the image processing apparatus 1. First, the arithmetic unit 2 acquires the luminal image to be processed (Step S1).

Figure 6:
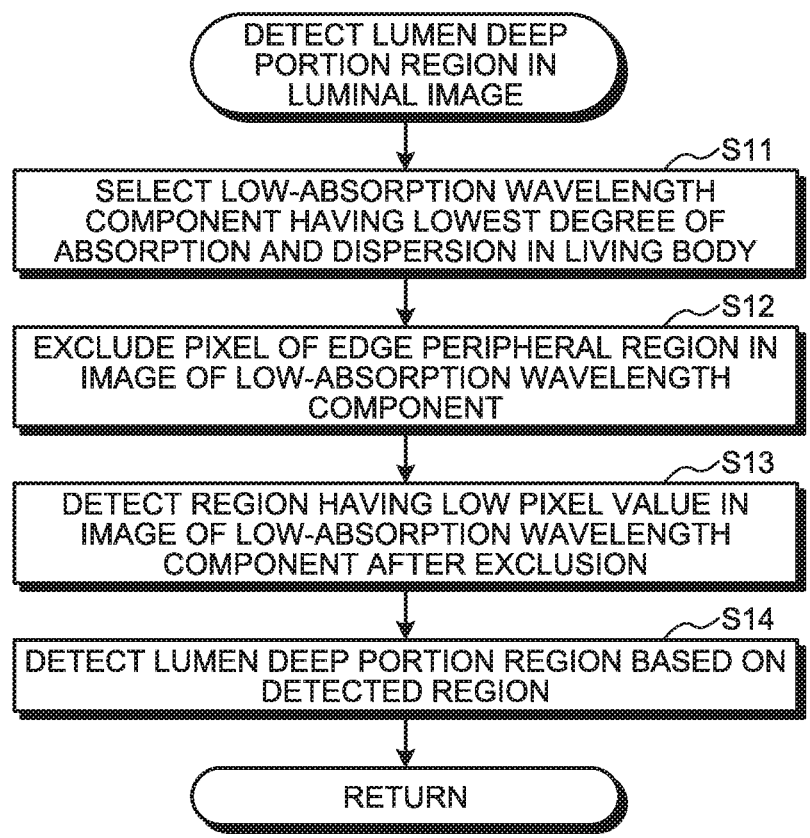
FIG. 6 is a flowchart illustrating an overview of a process performed by a lumen deep portion region detection unit of the image processing apparatus according to the first embodiment.

Subsequently, the lumen deep portion region detection unit 41 detects the lumen deep portion region in the luminal image (Step S2). FIG. 6 is a flowchart illustrating an overview of a process performed by the lumen deep portion region detection unit 41. Hereinafter, the processing of the lumen deep portion region detection unit 41 will be described with reference to FIG. 6. First, the low-absorption wavelength component selector 411 selects a low-absorption wavelength component having the lowest degree of absorption and dispersion in the living body (Step S11). The low-absorption wavelength component selector 411 selects the R component as described above, for example, in the case of the image composed of R, G and B components.

Thereafter, the edge peripheral region exclusion unit 412 excludes pixels in the edge peripheral region in the luminal image of the low-absorption wavelength component (Step S12). Accordingly, it is possible to prevent the edge peripheral region from being erroneously detected as the lumen deep portion region.

Subsequently, the low pixel value region detection unit 413 detects a region having a low pixel value, that is, a region of a pixel having a pixel value equal to or smaller than a predetermined threshold in an image of the low-absorption wavelength component after excluding the edge peripheral region (Step S13). Since the shooting distance is distant in the lumen deep portion as described above, the pixel value of the image of the low-absorption wavelength component is low.

Finally, the lumen deep portion region detection unit 41 detects the lumen deep portion region by performing the known labeling process or the like based on the region detected by the low pixel value region detection unit 413 (Step S14). Accordingly, a lumen deep portion region detection process (Step S2) performed by the lumen deep portion region detection unit 41 is ended.

Although the method of detecting the lumen deep portion region based on the pixel value correlating with the shooting distance has been described in the first embodiment, this is merely an example. For example, the lumen deep portion region may be detected based on a method described in JP 2003-93328 A or the like.

In addition, processing such as correction of unevenness in pixel value caused by an optical system or an illumination system, and removal of non-mucosal regions, such as specular reflection, residues, and bubbles, may be performed before performing the lumen deep portion region detection process. Accordingly, it is possible to suppress reduction in accuracy of each subsequent process.

In Step S3 subsequent to Step S2, the range setting unit 511 sets the range of the region to be used for the feature data calculation to detect the specific region according to presence or absence of the lumen deep portion region (Step S3).

Subsequently, the feature data calculation unit 51 sets a feature data calculation region of the set range to an arbitrary position in the luminal image, and calculates the feature data from within the region (Step S4).

Thereafter, the identification unit 52 identifies the region in the luminal image and detects the specific region (Step S5). The identification unit 52 calculates the identification index P(x) based on the probability model shown in the above-described Formula (1), for example, and identifies the region where the value thereof is equal to or larger than the threshold as the specific region.

Finally, the arithmetic unit 2 outputs a result of the detection of the specific region (Step S6). Accordingly, the image processing apparatus 1 ends a series of processes.

According to the first embodiment described above, it is possible to accurately detect the specific region by appropriately switching the global feature data calculation and the local feature data calculation since the range of the region to be used for the feature data calculation is set according to the presence or absence of the lumen deep portion region.

Modification 1-1

Figure 7:
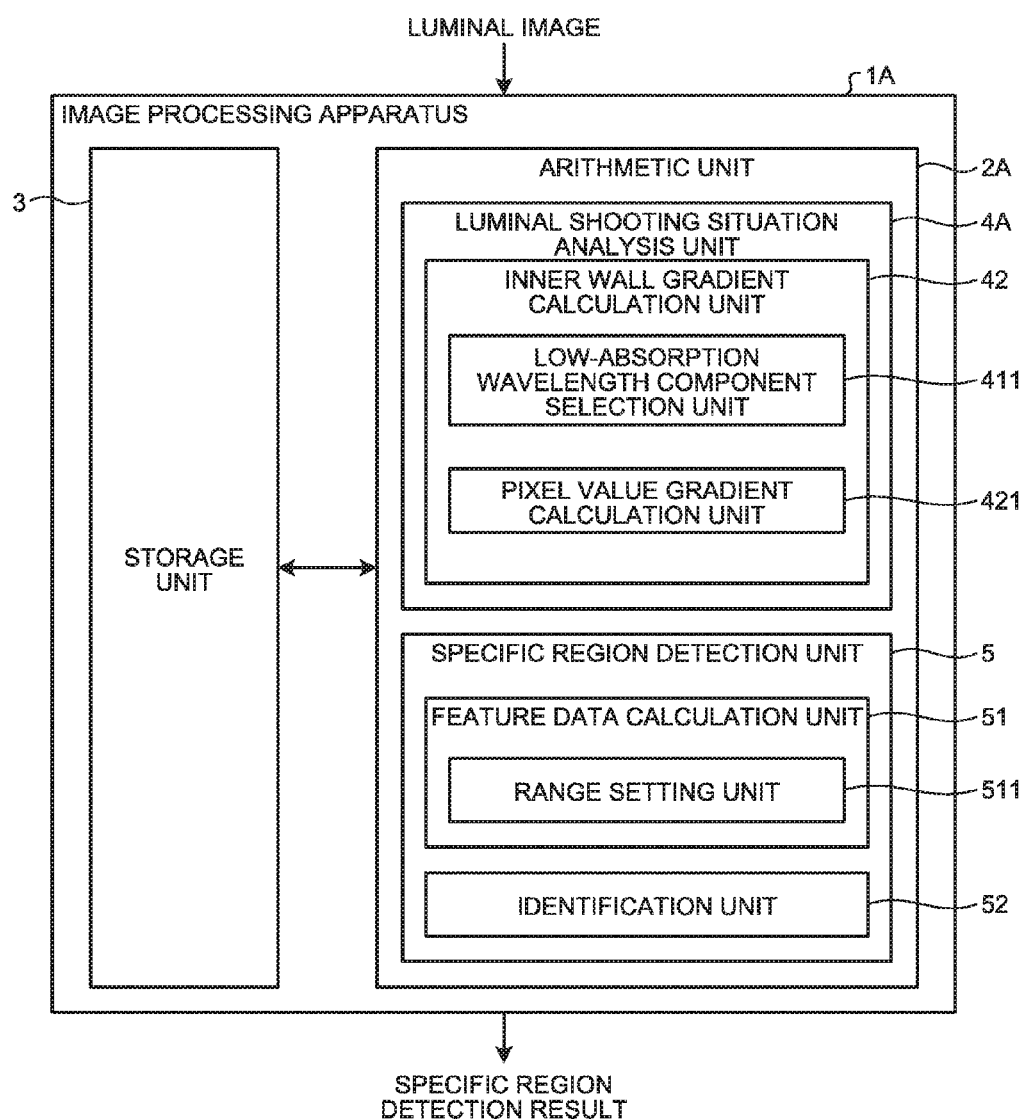
FIG. 7 is a block diagram illustrating a functional configuration of an image processing apparatus according to Modification 1-1 of the first embodiment.

FIG. 7 is a block diagram illustrating a functional configuration of an image processing apparatus according to Modification 1-1 of the first embodiment. In an image processing apparatus 1A illustrated in the same drawing, constituent parts having the same functions as those of the image processing apparatus 1 illustrated in FIG. 1 will be denoted by the same reference numerals as those in FIG. 1.

The image processing apparatus 1A includes an arithmetic unit 2A and the storage unit 3. The arithmetic unit 2A includes a luminal shooting situation analysis unit 4A and the specific region detection unit 5.

The luminal shooting situation analysis unit 4A includes an inner wall gradient calculation unit 42 that calculates a gradient of a luminal wall (inner wall gradient) in a luminal image. The inner wall gradient calculation unit 42 includes a low-absorption wavelength component selector 411 that selects a low-absorption wavelength component having the lowest degree of absorption and dispersion in a living body, and a pixel value gradient calculation unit 421 that calculates a pixel value gradient of the low-absorption wavelength component.

The pixel value gradient calculation unit 421 calculates a magnitude and a direction of the pixel value gradient based on a primary differential filter output $\Delta X$ in an X direction having a predetermined size and a primary differential filter output $\Delta Y$ in an Y direction having the same size (reference: CG-ARTS Society: Digital Image Processing: 115P, Differential Filter). The pixel value gradient calculation unit 421 may calculate the gradient of the luminal wall at each pixel position or at a predetermined sampling interval.

Figure 8:
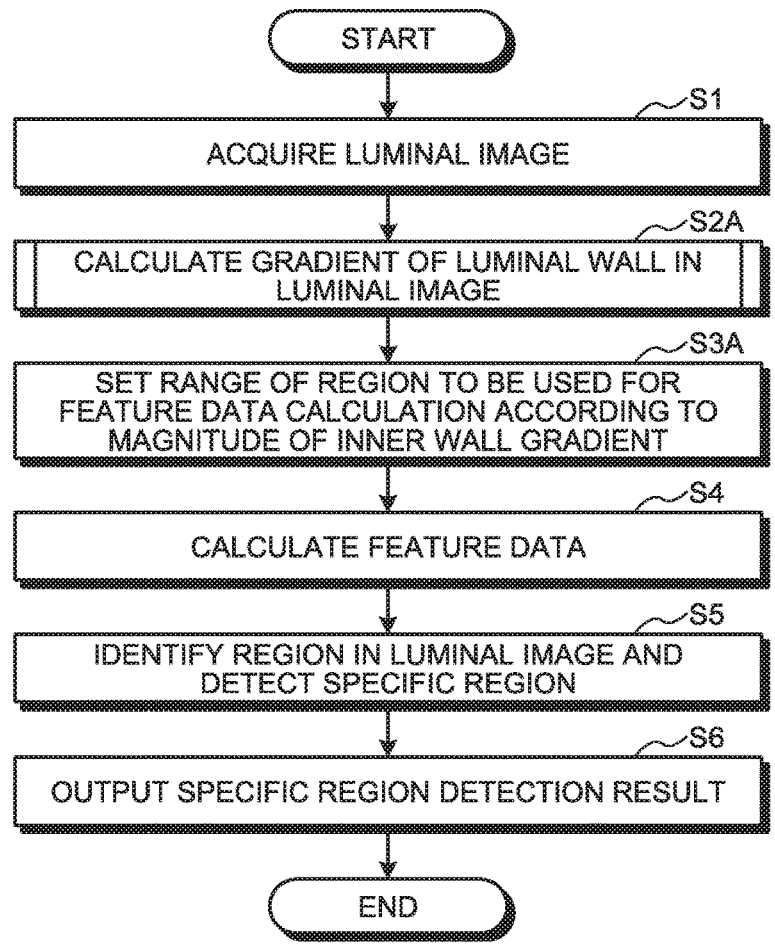
FIG. 8 is a flowchart illustrating an overview of a process performed by the image processing apparatus according to Modification 1-1 of the first embodiment.

FIG. 8 is a flowchart illustrating an overview of a process performed by the image processing apparatus 1A. In FIG. 8, the same step numbers are attached to the same processes as those of the flowchart illustrated in FIG. 5. Hereinafter, a process subsequent to Step S1 will be described.

Figure 9:
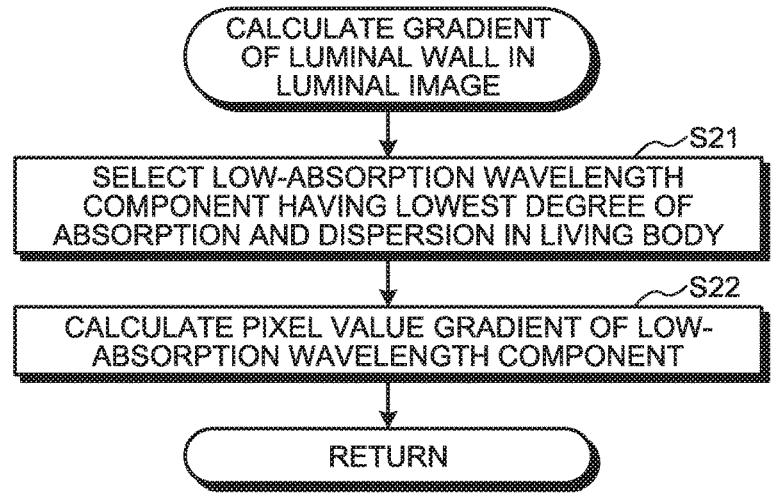
FIG. 9 is a flowchart illustrating an overview of a process performed by an inner wall gradient calculation unit of the image processing apparatus according to Modification 1-1 of the first embodiment.

In Step S2A, the inner wall gradient calculation unit 42 calculates the gradient of the luminal wall in the luminal image (Step S2A). FIG. 9 is a flowchart illustrating an overview of a process performed by the inner wall gradient calculation unit 42. Hereinafter, the processing of the inner wall gradient calculation unit 42 will be described with reference to FIG. 9. First, the low-absorption wavelength component selector 411 selects a low-absorption wavelength component having the lowest degree of absorption and dispersion in the living body (Step S21).

Subsequently, the pixel value gradient calculation unit 421 calculates the pixel value gradient of the selected low-absorption wavelength component (Step S22). Accordingly, the process of calculating the gradient of the luminal wall in the luminal image performed by the inner wall gradient calculation unit 42 (Step S2A) is ended.

After Step S2A, the range setting unit 511 sets the range of the region to be used for the feature data calculation in accordance with a magnitude of the inner wall gradient (Step S3A). A case where an average value of the magnitudes of the inner wall gradients calculated at a plurality of locations is equal to or larger than a predetermined threshold corresponds to a situation where the luminal wall is being shot obliquely. In this case, the range setting unit 511 sets the range of the region to be used for the feature data calculation to be relatively large. On the other hand, a case where the average value of the magnitudes of the inner wall gradients is smaller than the predetermined threshold corresponds to a situation where the luminal wall is being shot from the front. In this case, the range setting unit 511 sets the range of the region to be used for the feature data calculation to be smaller than that of the case where the average value of the magnitudes of the inner wall gradients is equal to or larger than the threshold.

The processes of Steps S4 to S6 subsequent to Step S3A are the same as the processes that have been described in the first embodiment.

According to Modification 1-1 of the first embodiment described above, it is possible to accurately detect the specific region by appropriately switching the global feature data calculation and the local feature data calculation since the range of the region to be used for the feature data calculation is set in accordance with the magnitude of the inner wall gradient.

Incidentally, the luminal shooting situation analysis unit 4A may be configured to further include the lumen deep portion region detection unit 41, which has been described in the first embodiment, in Modification 1-1. In this case, the range setting unit 511 sets the range of the region to be used for the feature data calculation according to the presence or absence of the lumen deep portion region and the magnitude of the inner wall gradient.

Modification 1-2

Figure 10:
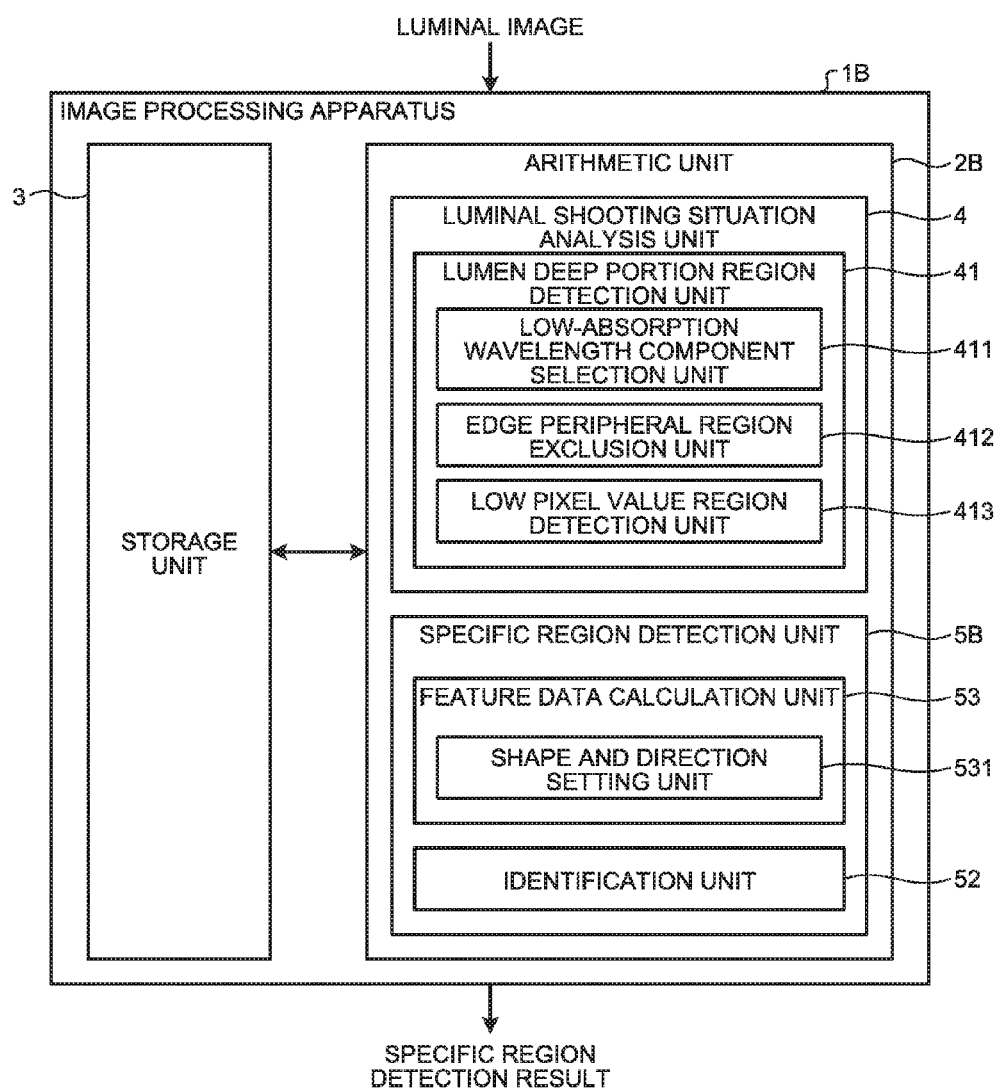
FIG. 10 is a block diagram illustrating a functional configuration of an image processing apparatus according to Modification 1-2 of the first embodiment.

FIG. 10 is a block diagram illustrating a functional configuration of an image processing apparatus according to Modification 1-2 of the first embodiment. In an image processing apparatus 1B illustrated in the same drawing, constituent parts having the same functions as those of the image processing apparatus 1 illustrated in FIG. 1 will be denoted by the same reference numerals as those in FIG. 1.

The image processing apparatus 1B includes an arithmetic unit 2B and the storage unit 3. The arithmetic unit 2B includes the luminal shooting situation analysis unit 4 and a specific region detection unit 5B.

The specific region detection unit 5B includes a feature data calculation unit 53 and the identification unit 52. The feature data calculation unit 53 includes a shape and direction setting unit 531 that sets a shape and/or a direction of a region to be used for calculation of feature data to detect a specific region. A case where the lumen deep portion region is present in the image corresponds to the situation where the luminal wall is being shot obliquely, and an abnormal region is likely to be reflected as an image that is short with respect to a direction (depth direction) of the deep portion region and long in a direction orthogonal to the direction of the lumen deep portion region as illustrated in FIG. 1. In this case, the shape and direction setting unit 531 sets the shape of the region to be used for the feature data calculation to a shape that is long in the direction orthogonal to the direction of the lumen deep portion region.

On the other hand, a case where the lumen deep portion region is not present in the image corresponds to the situation where the luminal wall is being shot from the front, and a change of the length of the image as in the case of obliquely shooting the luminal wall does not occur as illustrated in FIG. 2. In this case, the shape and direction setting unit 531 sets the shape of the region to be used for the feature data calculation to a shape that is not dependent on the direction or a substantially square shape.

Incidentally, an image also changes in a rotational direction according to a vertical direction of a shooting machine in the situation where the shooting is obliquely performed. Thus, when setting the direction of the region to be used for the feature data calculation, the shape and direction setting unit 531 may perform rotation correction such that the direction of the region is aligned in the direction of the lumen deep portion region. When being set in this manner, the processing of the identification unit 52 in the subsequent stages may be made common with respect to a specific region whose shape changes in the rotational direction.

Figure 11:
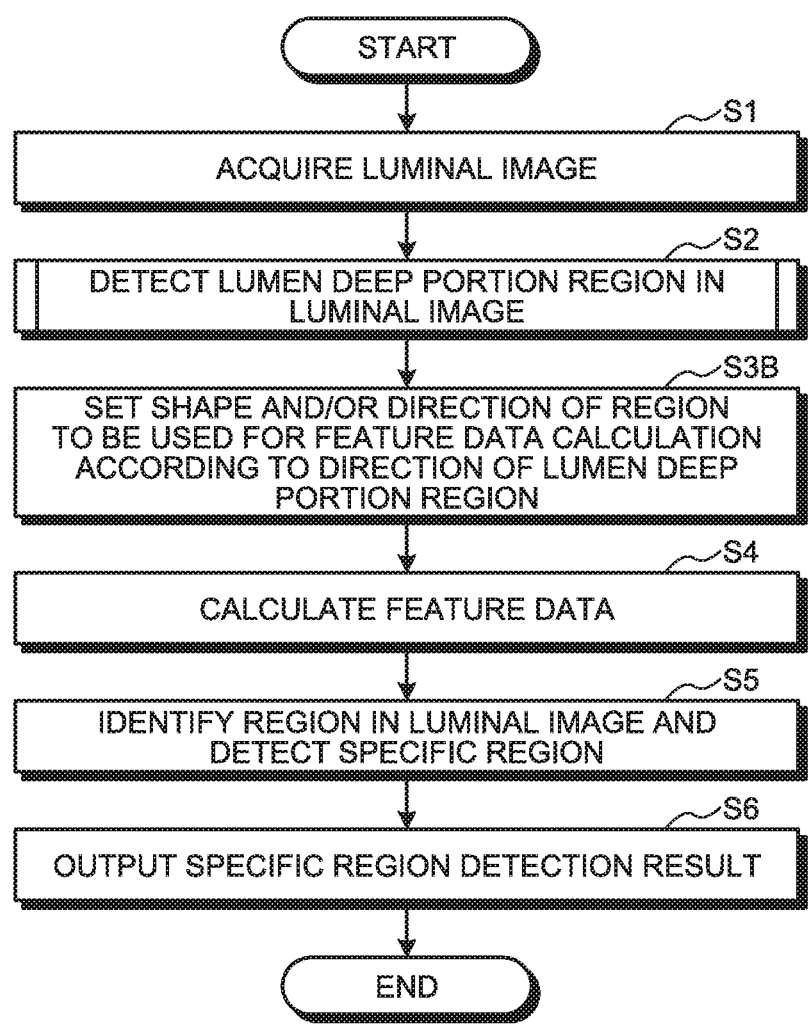
FIG. 11 is a flowchart illustrating an overview of a process performed by the image processing apparatus according to Modification 1-2 of the first embodiment.

FIG. 11 is a flowchart illustrating an overview of a process performed by the image processing apparatus 1B. In FIG. 11, the same step numbers are attached to the same processes as those of the flowchart illustrated in FIG. 5. Hereinafter, a process subsequent to Step S2 will be described.

In Step S3B, the shape and direction setting unit 531 sets the shape and/or direction of the region to be used for the feature data calculation in accordance with the direction of the lumen deep portion region (Step S3B).

Thereafter, the feature data calculation unit 53 sets the feature data calculation region having the set shape and/or direction to an arbitrary position in the luminal image, and calculates the feature data from within the region (Step S4). The processes of Steps S5 and S6 subsequent to Step S4 are the same as the processes that have been described in the first embodiment.

According to Modification 1-2 described above, it is possible to set the feature data calculation region, which is adaptive to the change of the image caused by the difference (oblique or front) in the shooting direction with respect to the luminal wall and suppressed in waste in the amount of operation and mixing of the region leading to reduction in accuracy (specular reflection, residues, bubbles, normal folds, and the like), and to accurately detect the specific region since the shape and/or direction of the region to be used for the feature data calculation is set in accordance with the direction of the lumen deep portion region.

Incidentally, the image processing apparatus 1B may be also configured to include the luminal shooting situation analysis unit 4A, which has been described in Modification 1-1, instead of including the luminal shooting situation analysis unit 4 in Modification 1-2. In this case, the shape and direction setting unit 531 sets the shape and/or direction of the region to be used for the feature data calculation in accordance with the direction of the inner wall gradient.

In addition, the luminal shooting situation analysis unit 4 may be configured to further include the inner wall gradient calculation unit 42, which has been described in Modification 1-1, in Modification 1-2. In this case, the shape and direction setting unit 531 sets the shape and/or direction of the region to be used for the feature data calculation in accordance with the direction of the lumen deep portion region and the direction of the inner wall gradient.

Modification 1-3

Figure 12:
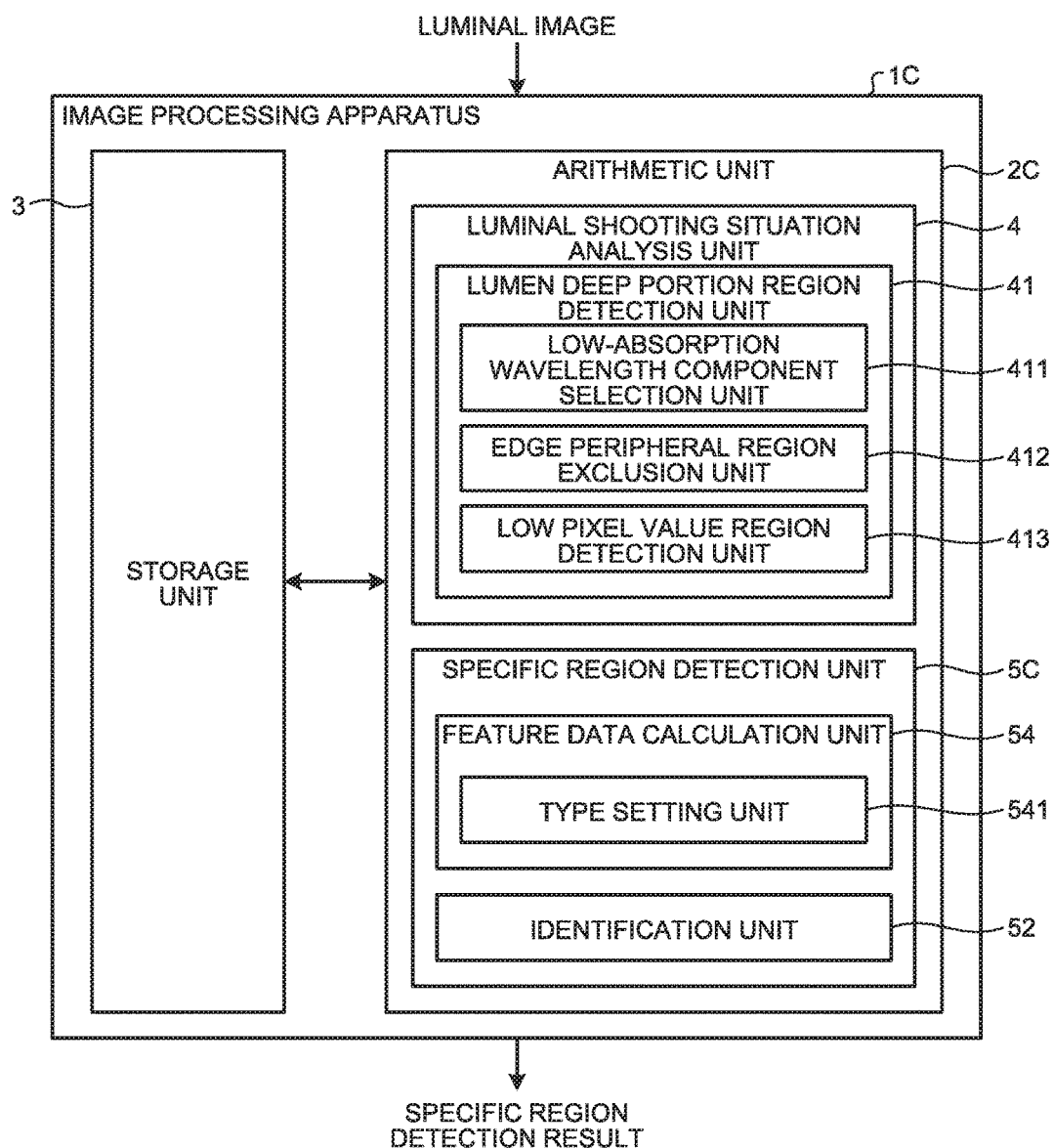
FIG. 12 is a block diagram illustrating a functional configuration of an image processing apparatus according to Modification 1-3 of the first embodiment.

FIG. 12 is a block diagram illustrating a functional configuration of an image processing apparatus according to Modification 1-3 of the first embodiment. In an image processing apparatus 1C illustrated in the same drawing, constituent parts having the same functions as those of the image processing apparatus 1 illustrated in FIG. 1 will be denoted by the same reference numerals as those in FIG. 1.

The image processing apparatus 1C includes an arithmetic unit 2C and the storage unit 3. The arithmetic unit 2C includes the luminal shooting situation analysis unit 4 and a specific region detection unit 5C.

The specific region detection unit 5C includes a feature data calculation unit 54 and the identification unit 52. The feature data calculation unit 54 includes a type setting unit 541 that sets a type of feature data to be used for detection of a specific region or a weight of feature data for each type.

The type setting unit 541 sets the type of the feature data to be used for detection of the specific region or the weight of the feature data for each type according to presence or absence of the lumen deep portion region in the luminal image. A case where the lumen deep portion region is present in the luminal image corresponds to a situation where the luminal wall is being shot obliquely, and thus, a contour line of an abnormal region surface becomes clear (see FIG. 1). In this case, the type setting unit 541 sets use of contour feature data among feature data of a color, a contour, a pixel value surface shape, texture, and the like, and sets a higher weight to the contour feature data among a plurality of types of feature data than the other types of feature data. The type setting unit 541 performs known feature axis normalization (linear transformation such that an average becomes zero and a variance becomes one) with respect to the plurality of types of calculated feature data, and then, multiplies a coefficient such that only a variance of the contour feature data becomes larger than one.

On the other hand, a case where the lumen deep portion region is not present in the luminal image corresponds to a situation where the luminal wall is being shot from the front, and the contour line of the abnormal region surface is likely to be unclear as compared to the situation of being obliquely shot (see FIG. 2). However, the pixel value surface shape (pixel value gradient) and the texture are easily captured. In this case, the type setting unit 541 sets use of pixel value surface shape feature data or texture feature data among the feature data of the color, the contour, the pixel value surface shape, the texture, and the like, or sets a higher weight to the pixel value surface shape feature data or the texture feature data among the plurality of types of feature data than the other types of feature data.

Figure 13:
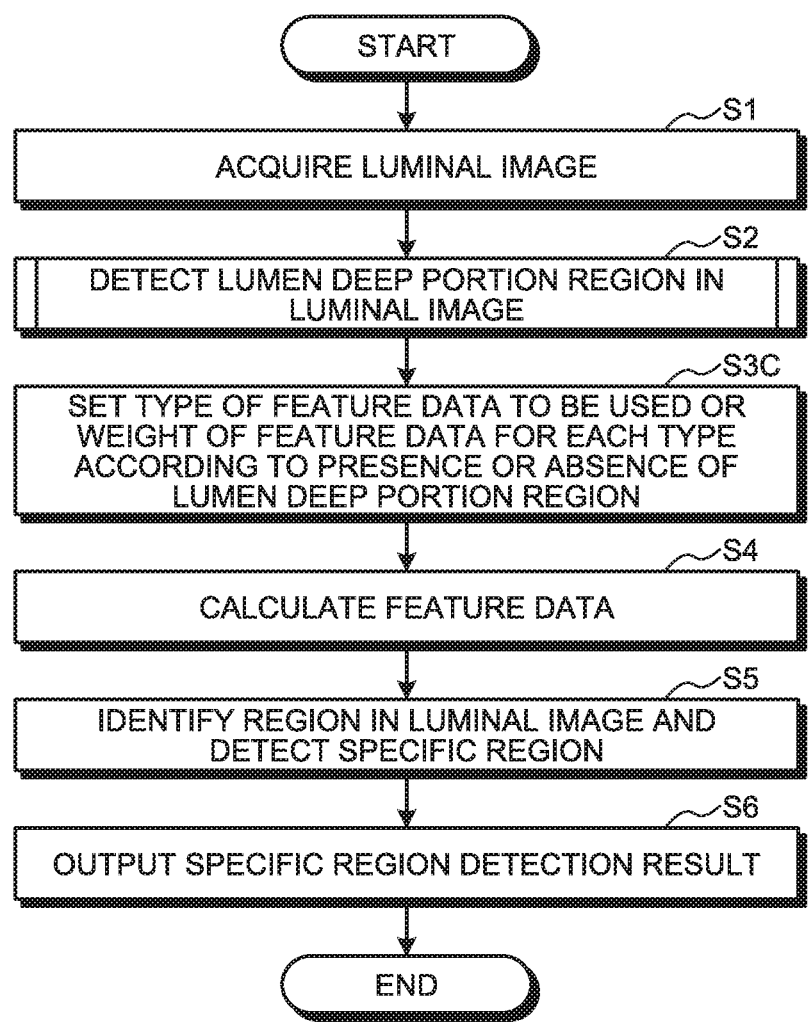
FIG. 13 is a flowchart illustrating an overview of a process performed by the image processing apparatus according to Modification 1-3 of the first embodiment.

FIG. 13 is a flowchart illustrating an overview of a process performed by the image processing apparatus 1C. In FIG. 13, the same step numbers are attached to the same processes as those of the flowchart illustrated in FIG. 5. Hereinafter, a process subsequent to Step S2 will be described.

In Step S3C, the type setting unit 541 sets the type of the feature data to be used or the weight of the feature data for each type according to the presence or absence of the lumen deep portion region in the luminal image (Step S3C).

Thereafter, the feature data calculation unit 54 sets the feature data calculation region at an arbitrary position in the luminal image, and calculates the feature data from within that region (Step S4). The processes of Steps S5 and S6 subsequent to Step S4 are the same as the processes that have been described in the first embodiment.

According to Modification 1-3 described above, it is possible to perform the feature data calculation, which is adaptive to the change of the feature data caused by the difference (oblique or front) in the shooting direction with respect to the luminal wall to put emphasis on the feature data that is clearer, and to accurately detect the specific region since the feature data to be used or the feature data to be emphasized is set in accordance with the presence or absence of the lumen deep portion region.

Incidentally, the image processing apparatus 1C may be also configured to include the luminal shooting situation analysis unit 4A, which has been described in Modification 1-1, instead of including the luminal shooting situation analysis unit 4 in Modification 1-3. In this case, the type setting unit 541 sets the type of the feature data to be used or the weight of the feature data for each type in accordance with a magnitude of an inner wall gradient.

A case where an average value of magnitudes of inner wall gradients is equal to or larger than a predetermined threshold corresponds to a situation where the luminal wall is being shot obliquely. In this case, the type setting unit 541 sets use of the contour feature data among the feature data of the color, the contour, the pixel value surface shape, the texture, and the like, or sets a high weight to the contour feature data among the plurality of types of feature data.

On the other hand, a case where the average value of the magnitudes of the inner wall gradients is smaller than the predetermined threshold corresponds to a situation where the luminal wall is being shot from the front. In this case, the type setting unit 541 sets use of the pixel value surface shape feature data or the texture feature data among the feature data of the color, the contour, the pixel value surface shape, the texture, and the like, or sets a high weight to the pixel value surface shape feature data or the texture feature data among the plurality of types of feature data.

The luminal shooting situation analysis unit 4 may be configured to further include the inner wall gradient calculation unit 42, which has been described in Modification 1-1, in Modification 1-3. In this case, the type setting unit 541 sets the feature data to be used or the feature data to be emphasized according to the presence or absence of the lumen deep portion region and the magnitude of the inner wall gradient, and thus, the specific region is detected more accurately.

Second Embodiment

Figure 14:
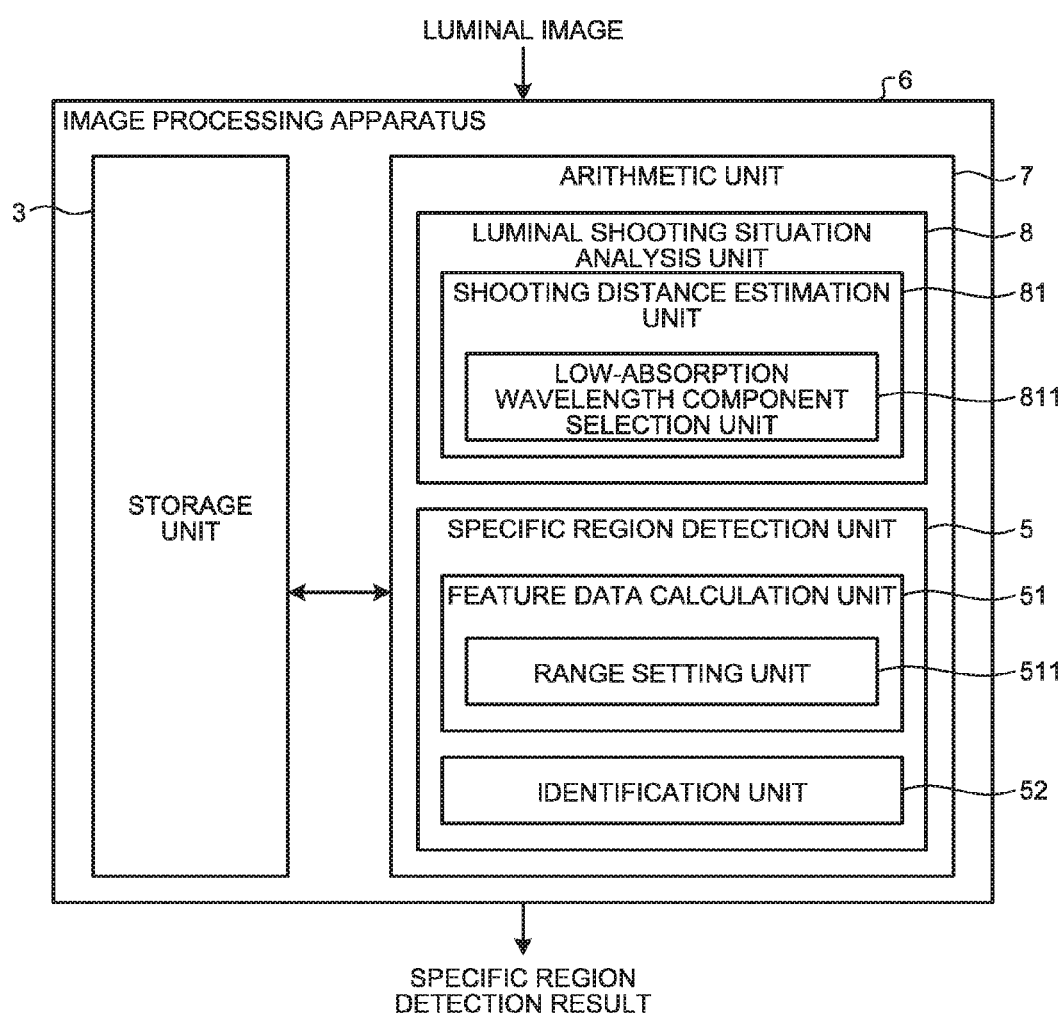
FIG. 14 is a block diagram illustrating a functional configuration of an image processing apparatus according to a second embodiment.

FIG. 14 is a block diagram illustrating a functional configuration of an image processing apparatus according to a second embodiment. In an image processing apparatus 6 illustrated in the same drawing, constituent parts having the same functions as those of the image processing apparatus 1 illustrated in FIG. 3 will be denoted by the same reference numerals as those in FIG. 3.

The image processing apparatus 6 includes an arithmetic unit 7 and the storage unit 3. The arithmetic unit 7 includes a luminal shooting situation analysis unit 8 and the specific region detection unit 5.

The luminal shooting situation analysis unit 8 includes a shooting distance estimation unit 81 that estimates a shooting distance to a luminal wall. Various methods have been known as a method of performing shooting distance estimation. In the second embodiment, a method of estimating the shooting distance assuming an object to be shot as a uniform diffused surface will be described as an example.

The shooting distance estimation unit 81 includes a low-absorption wavelength component selector 811 that selects a low-absorption wavelength component having the lowest degree of absorption and dispersion in a living body. Such a configuration aims to suppress a decrease of a pixel value caused by to a blood vessel or the like reflected on a mucosal surface and to obtain pixel value information correlating with the shooting distance to the mucosal surface the most. The R component is selected as described in the first embodiment, for example, in the case of the image composed of R, G and B components.

The shooting distance estimation unit 81 estimates the shooting distance assuming the uniform diffused surface based on the pixel value of the selected low-absorption wavelength component. Specifically, the shooting distance estimation unit 81 estimates a shooting distance r at a plurality of locations in the luminal image according to the following Formula (2).

$$r = \sqrt{\frac{I \times K \times \cos\theta}{L}} \quad (2)$$

Here, I on the right side of the Formula (2) is a radiation intensity of a light source measured in advance, K is a diffuse reflection coefficient of the mucosal surface, θ is an angle between a normal vector of the mucosal surface and a vector from the surface to the light source, and L is an R component value of a pixel in which the mucosal surface as a target of shooting distance estimation is reflected. Among these, the diffuse reflection coefficient K is obtained by measuring an average value in advance. In addition, an average value is set in advance for the angle θ as a value determined by a positional relationship between a distal end of an endoscope and the mucosal surface in advance.

Incidentally, the shooting distance estimation unit 81 may be configured to perform adaptive processing at the subsequent stages using a pixel value having correlation with the shooting distance r instead of estimating the shooting distance r defined by Formula (2).

A case where an average value of shooting distances calculated by the shooting distance estimation unit 81 at the plurality of locations is smaller than a predetermined threshold corresponds to a situation where the shooting distance is relatively close. When the shooting distance is close, the subject is reflected to be larger than a case where the shooting distance is distant. In this case, the range setting unit 511 sets the range of the region to be used for the feature data calculation to be relatively large.

On the other hand, a case where the average value of the shooting distances is equal to or larger than the predetermined threshold corresponds to a situation where the shooting distance is relatively distant. Since the subject is reflected to be relative small under this situation, it is likely to cause waste in the amount of operation and mixing of a region that lead to reduction in accuracy (specular reflection, residues, bubbles, normal folds, and the like) if a range of a region to be used for feature data calculation is set to be large. In this case, the range setting unit 511 sets the range of the region to be used for the feature data calculation to be smaller than that of the case where the average value of the shooting distances is smaller than the threshold.

Figure 15:
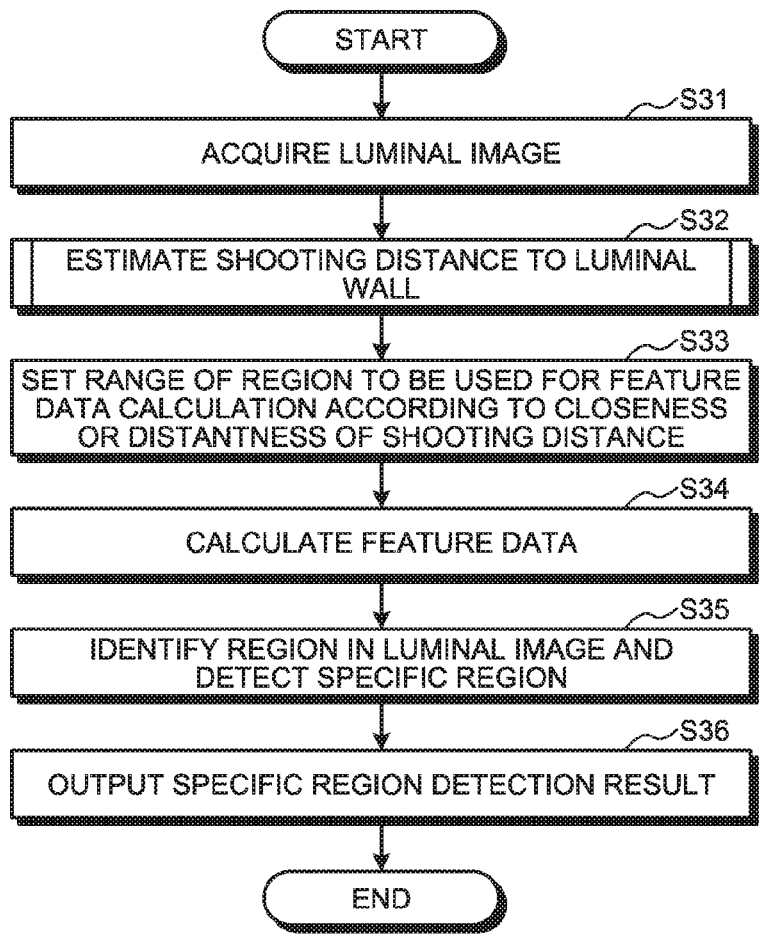
FIG. 15 is a flowchart illustrating an overview of a process performed by the image processing apparatus according to the second embodiment.

FIG. 15 is a flowchart illustrating an overview of a process executed by the image processing apparatus 6. First, the arithmetic unit 7 acquires the luminal image to be processed (Step S31).

Figure 16:
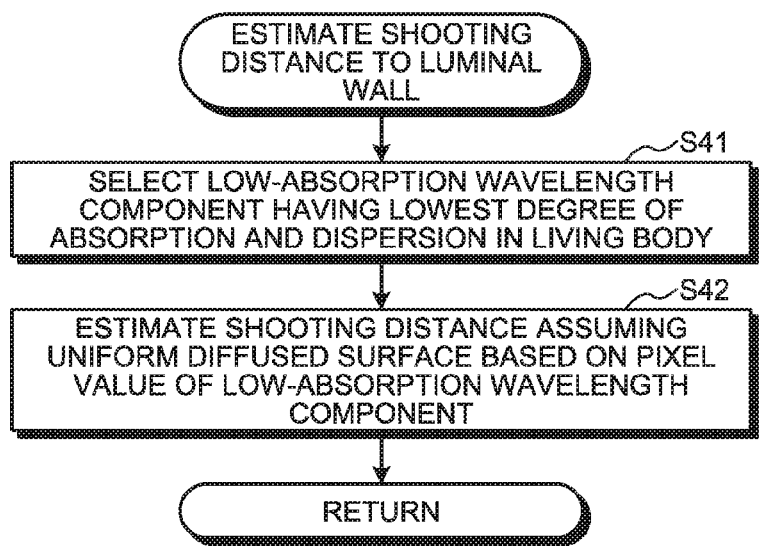
FIG. 16 is a flowchart illustrating an overview of a process performed by a shooting distance estimation unit of the image processing apparatus according to the second embodiment.

Subsequently, the shooting distance estimation unit 81 estimates the shooting distance to the luminal wall (Step S32). FIG. 16 is a flowchart illustrating an overview of a process performed by the shooting distance estimation unit 81. Hereinafter, the processing of the shooting distance estimation unit 81 will be described with reference to FIG. 16. First, the low-absorption wavelength component selector 811 selects a low-absorption wavelength component having the lowest degree of absorption and dispersion in the living body (Step S41).

Thereafter, the shooting distance estimation unit 81 estimates the shooting distance assuming the uniform diffused surface based on the pixel value of the selected low-absorption wavelength component (Step S42). Specifically, the shooting distance estimation unit 81 estimates the shooting distance according to the above-described Formula (2). Accordingly, the shooting distance estimation process (Step S32) performed by the shooting distance estimation unit 81 is ended.

Incidentally, the arithmetic unit 7 may perform processing such as correction of unevenness in pixel value caused by an optical system or an illumination system, and removal of non-mucosal regions, such as specular reflection, residues, and bubbles, before the shooting distance estimation unit 81 performs the shooting distance estimation process. Accordingly, it is possible to suppress reduction in accuracy of each subsequent process.

In addition, a detection means such as a distance measurement sensor may be provided in an endoscope such that the shooting distance estimating unit 81 estimates the shooting distance based on a result of such detection.

After Step S32, the range setting unit 511 sets a range of a region to be used for feature data calculation according to closeness or distantness of the estimated shooting distance (Step S33).

The processes of Steps S35 and S36 performed subsequently to Step S34 are the same as the processes of Steps S5 and S6 that have been described in the first embodiment, respectively.

According to the second embodiment described above, it is possible to set the feature data calculation region, which is adaptive to a change of the luminal image caused by a difference in shooting situation, and to accurately detect the specific region since the range of the region to be used for the feature data calculation is set according to the closeness or distantness of the shooting distance.

Modification 2-1

Figure 17:
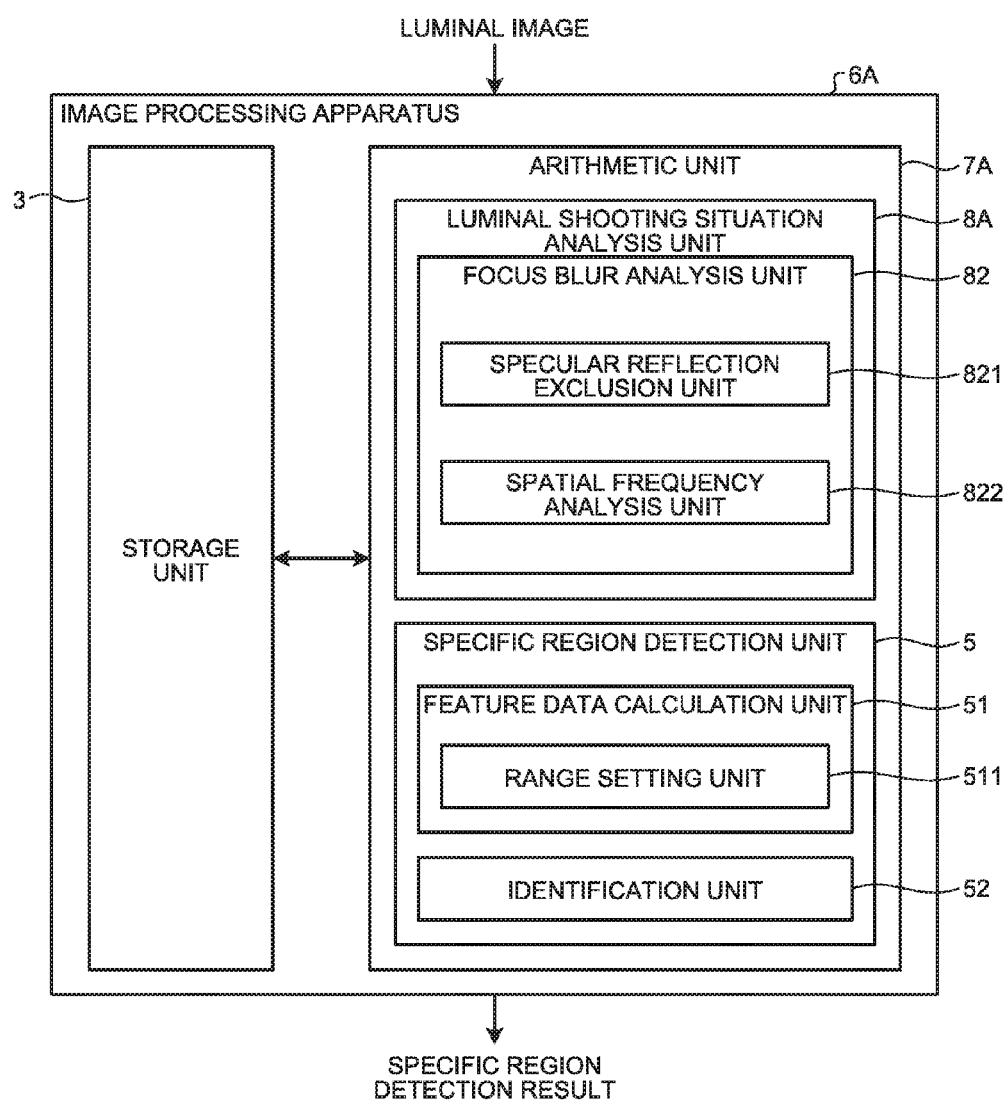
FIG. 17 is a block diagram illustrating a functional configuration of an image processing apparatus according to Modification 2-1 of the second embodiment.

FIG. 17 is a block diagram illustrating a functional configuration of an image processing apparatus according to Modification 2-1 of the second embodiment. In an image processing apparatus 6A illustrated in the same drawing, constituent parts having the same functions as those of the image processing apparatus 6 illustrated in FIG. 14 will be denoted by the same reference numerals as those in FIG. 14.

The image processing apparatus 6A includes an arithmetic unit 7A and the storage unit 3. The arithmetic unit 7A includes a luminal shooting situation analysis unit 8A and the specific region detection unit 5.

The luminal shooting situation analysis unit 8A includes a focus blur analysis unit 82 that analyzes a focus blur in a luminal image. The focus blur analysis unit 82 includes a specular reflection exclusion unit 821 and a spatial frequency analysis unit 822.

The specular reflection exclusion unit 821 discriminates and excludes specular reflection in the luminal image, for example, based on a method disclosed in JP 2012-11137 A.

The spatial frequency analysis unit 822 obtains a Fourier spectrum by performing known two-dimensional Fourier transformation (reference: CG-ARTS Society: Digital Image Processing: 128P, Two-Dimensional Fourier Transformation) on a predetermined component (for example, a G component or the like) of the luminal image, and then, obtains radial distribution by calculating the sum of spectra in an annular region where a distance from the center representing a low frequency component falls within a predetermined range while changing the distance. In this radial distribution, a portion with a small distance represents the low frequency component of the luminal image and a portion with a large distance represents a high frequency component of the luminal image. In general, a focus blur is large in an image with few high frequency components.

FIG. 18 is a flowchart illustrating an overview of a process performed by the image processing apparatus 6A. In FIG. 18, the same step numbers are attached to the same processes as those of the flowchart illustrated in FIG. 15. Hereinafter, a process subsequent to Step S31 will be described.

In Step S32A, the focus blur analysis unit 82 analyzes a focus blur state of the luminal image (Step S32A). FIG. 19 is a flowchart illustrating an overview of a process performed by the focus blur analysis unit 82. Hereinafter, the processing of the focus blur analysis unit 82 will be described with reference to FIG. 19. First, the specular reflection exclusion unit 821 discriminates and excludes the specular reflection in the luminal image (Step S51).

Subsequently, the spatial frequency analysis unit 822 performs the two-dimensional Fourier transformation on the predetermined component of the luminal image, and then, calculates the radial distribution of the two-dimensional Fourier spectrum obtained by the two-dimensional Fourier transformation (Step S52).

Finally, the focus blur analysis unit 82 analyzes the focus blur state based on the radial distribution of the two-dimensional Fourier spectrum (Step S53). Specifically, the focus blur analysis unit 82 determines that a degree of the focus blur is larger as the number of high frequency components (a portion with a large distance in the radial distribution) in the luminal image is smaller.

After Step S32A, the range setting unit 511 sets a range of a region to be used for feature data calculation in accordance with the degree of the focus blur (Step S33A). When the degree of the focus blur is large, a subject image becomes an image of a wider range than a case where the degree of the focus blur is small. The range setting unit 511 sets the range of the region to be used for the feature data calculation to be larger as the degree of the focus blur increases.

The processes of Steps S34 to S36 subsequent to Step S33A are the same as the processes that have been described in the second embodiment.

According to Modification 2-1 described above, it is possible to set the feature data calculation region, which is adaptive to a change of the luminal image caused by a difference in shooting situation, and to accurately detect the specific region since the range of the region to be used for the feature data calculation is set in accordance with the degree of the focus blur.

Incidentally, the luminal shooting situation analysis unit 8A may be configured to further include the shooting distance estimation unit 81, which has been described in the second embodiment, in Modification 2-1. In this case, the range setting unit 511 sets the range of the region to be used for the feature data calculation according to closeness or distantness of the shooting distance and the degree of the focus blur.

Modification 2-2

Figure 20:
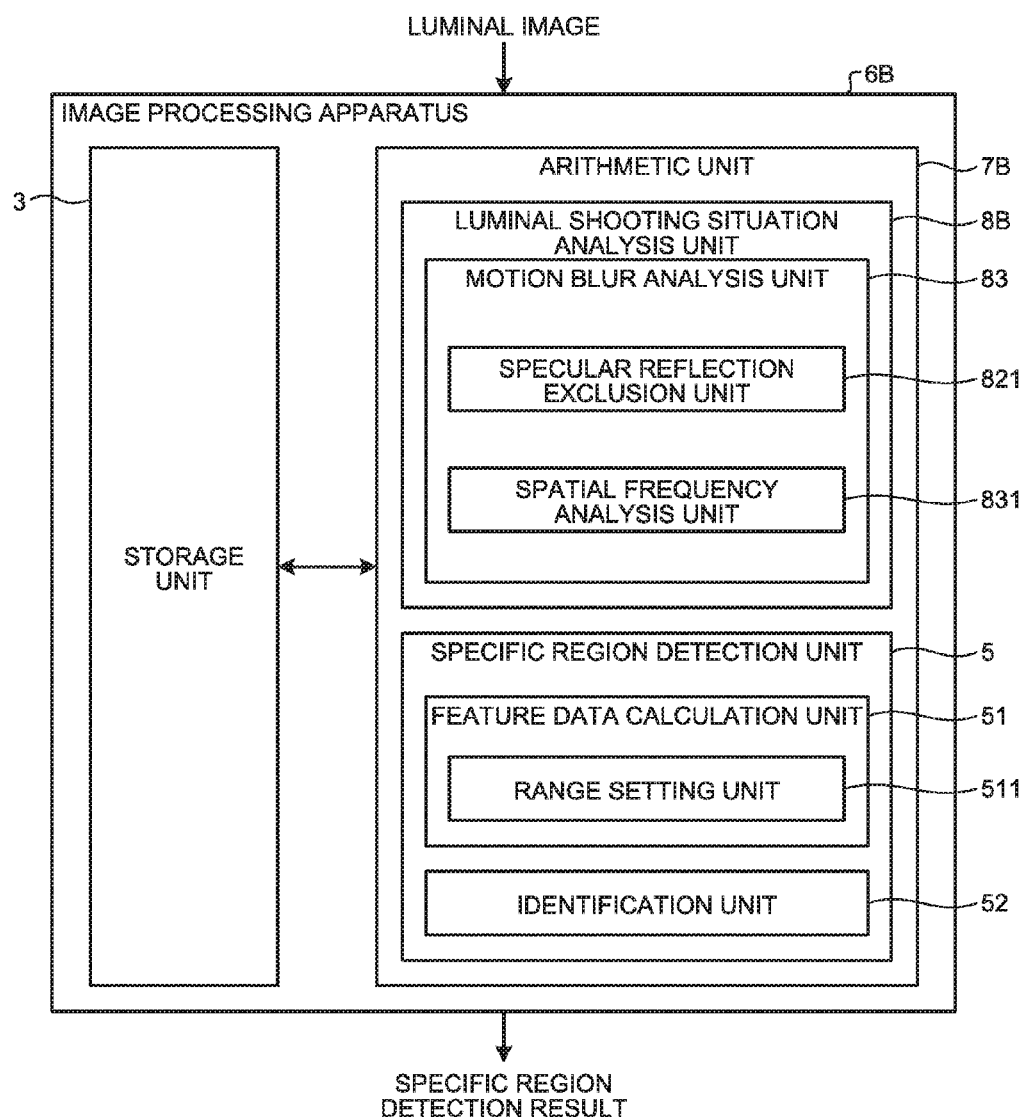
FIG. 20 is a block diagram illustrating a functional configuration of an image processing apparatus according to Modification 2-2 of the second embodiment.

FIG. 20 is a block diagram illustrating a functional configuration of an image processing apparatus according to Modification 2-2 of the second embodiment. In an image processing apparatus 6B illustrated in the same drawing, constituent parts having the same functions as those of the image processing apparatus 6A illustrated in FIG. 17 will be denoted by the same reference numerals as those in FIG. 17.

The image processing apparatus 6B includes an arithmetic unit 7B and the storage unit 3. The arithmetic unit 7B includes a luminal shooting situation analysis unit 8B and the specific region detection unit 5.

The luminal shooting situation analysis unit 8B includes a motion blur analysis unit 83 that analyzes a motion blur in a luminal image. The motion blur analysis unit 83 includes the specular reflection exclusion unit 821 and a spatial frequency analysis unit 831.

The spatial frequency analysis unit 831 calculates angular distribution and radial distribution of a two-dimensional Fourier spectrum. Specifically, the spatial frequency analysis unit 831 obtains the two-dimensional Fourier spectrum by performing two-dimensional Fourier transformation on a predetermined component (for example, a G component or the like) of the luminal image, and then, obtains the angular distribution by calculating the sum of spectra in a fan-shaped region where an angle with respect to a horizontal line passing through the center representing a low frequency component falls within a predetermined range while changing the angle. In addition, the spatial frequency analysis unit 831 obtains the radial distribution inside the fan-shaped region where the angle falls within the predetermined range using the same method as that described in Modification 2-1 inside the fan-shaped region where the angle falls within the predetermined range.

Figure 21:
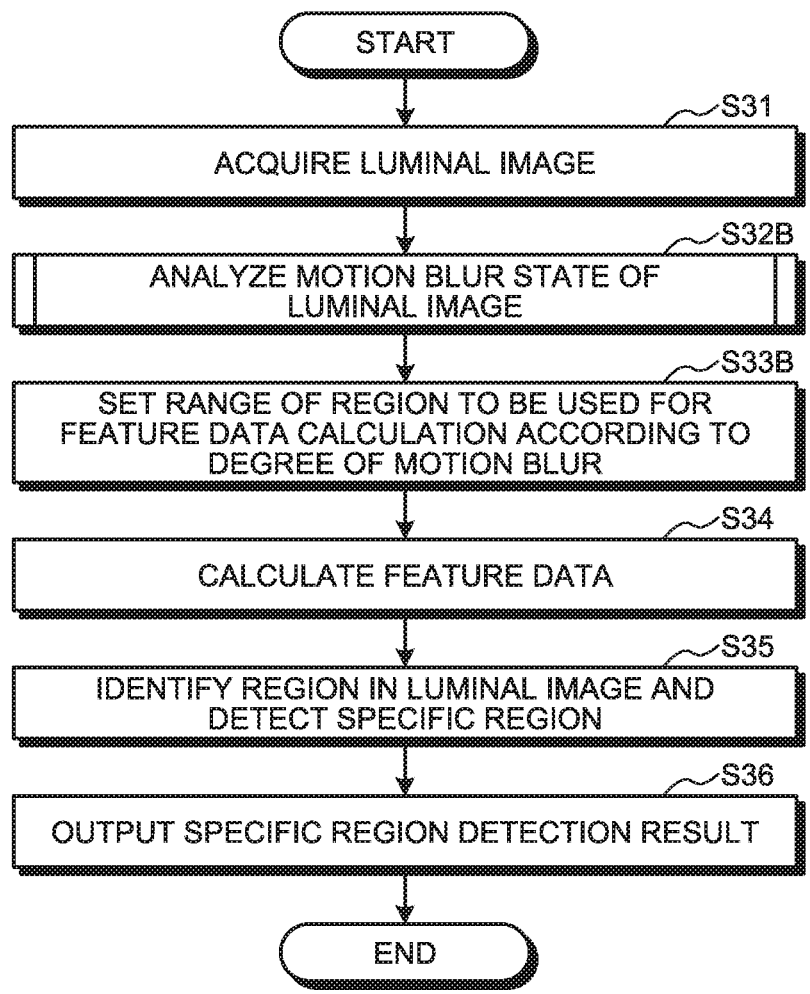
FIG. 21 is a flowchart illustrating an overview of a process performed by the image processing apparatus according to Modification 2-2 of the second embodiment.

FIG. 21 is a flowchart illustrating an overview of a process performed by the image processing apparatus 6B. In FIG. 21, the same step numbers are attached to the same processes as those of the flowchart illustrated in FIG. 15. Hereinafter, a process subsequent to Step S31 will be described.

Figure 22:
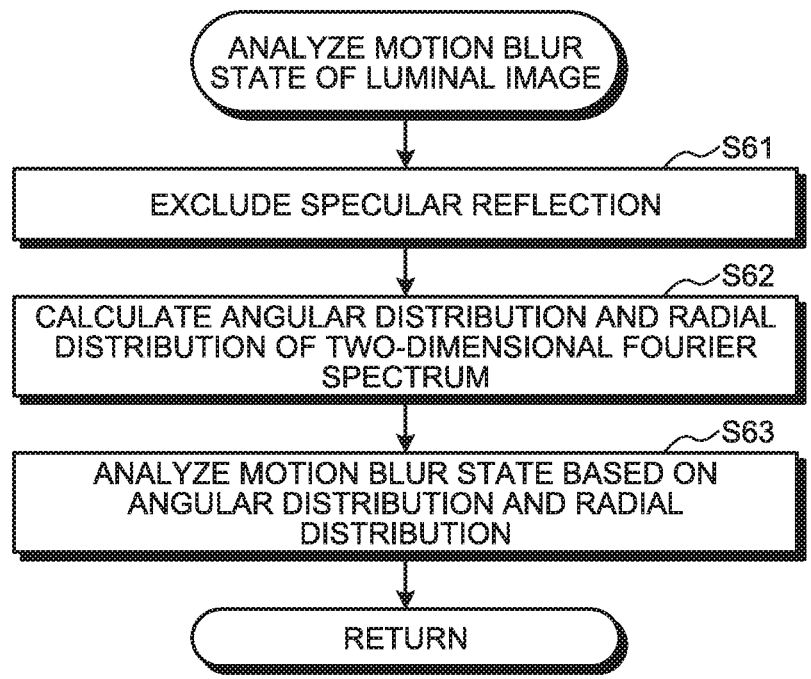
FIG. 22 is a flowchart illustrating an overview of a process performed by a motion blur analysis unit of the image processing apparatus according to Modification 2-2 of the second embodiment.

In Step S32B, the motion blur analysis unit 83 analyzes a motion blur state of the luminal image (Step S32B). FIG. 22 is a flowchart illustrating an overview of a process performed by the motion blur analysis unit 83. Hereinafter, the processing of the motion blur analysis unit 83 will be described with reference to FIG. 22. First, the specular reflection exclusion unit 821 excludes specular reflection in the luminal image (Step S61).

Subsequently, the spatial frequency analysis unit 831 calculates the angular distribution and the radial distribution of the two-dimensional Fourier spectrum (Step S62).

The motion blur analysis unit 83 analyzes the motion blur state based on the angular distribution and the radial distribution (Step S63). Specifically, the motion blur analysis unit 83 analyzes a direction of the motion blur based on the angular distribution and analyzes the motion blur state based on the radial distribution of a region obtained by narrowing the angle in accordance with an analysis result thereof. For example, when the motion blur occurs in a substantially constant direction, an angular direction corresponding to the direction causes a relatively high spectrum distribution. In this case, the motion blur analysis unit 83 analyzes the motion blur state based on the radial distribution near a region where the spectrum distribution is relatively high.

There is a shooting scheme that is called a frame sequential scheme in an endoscope. In this case, the shooting is performed using one image sensor while sequentially emitting illumination light of R, G and B along the time series. Thus, there are both a case where wavelength components causing the motion blur are limited only to any one component and a case where the motion blur occurs among wavelength components. Therefore, the motion blur analysis unit 83 analyzes the motion blur with each wavelength component of R, G and B, and further, analyzes the motion blur among the wavelength components in the case of the frame sequential scheme. The analysis of the motion blur among the wavelength components may be performed by generating a composite image by taking the sum of images of the wavelength components and performing the above-described spatial frequency analysis or the like on the composite image.

After Step S32B, the range setting unit 511 sets a range of a region to be used for feature data calculation in accordance with a direction and a degree of the motion blur (Step S33B). When the degree of the motion blur is large, a subject image becomes an image of a wider range than a case where the degree of the motion blur is small. The range setting unit 511 sets the range of the region to be used for the feature data calculation to be larger as the degree of the motion blur increases.

The processes of Steps S34 to S36 subsequent to Step S33B are the same as the processes that have been described in the second embodiment.

According to Modification 2-2 described above, it is possible to set the feature data calculation region, which is adaptive to a change of the luminal image caused by a difference in shooting situation, and to accurately detect the specific region since the range of the region to be used for the feature data calculation is set in accordance with the state (direction and degree) of the motion blur.

Incidentally, the process of excluding the specular reflection is not necessarily performed in Modification 2-2.

Incidentally, the luminal shooting situation analysis unit 8B may be configured to further include the shooting distance estimation unit 81, which has been described in the second embodiment, and/or the focus blur analysis unit 82, which has been described in Modification 2-1, in Modification 2-2. In this case, the range setting unit 511 sets the range of the region to be used for the feature data calculation according to closeness or distantness of the shooting distance and/or the degree of the focus blur, and the degree of the motion blur.

Modification 2-3

Figure 23:
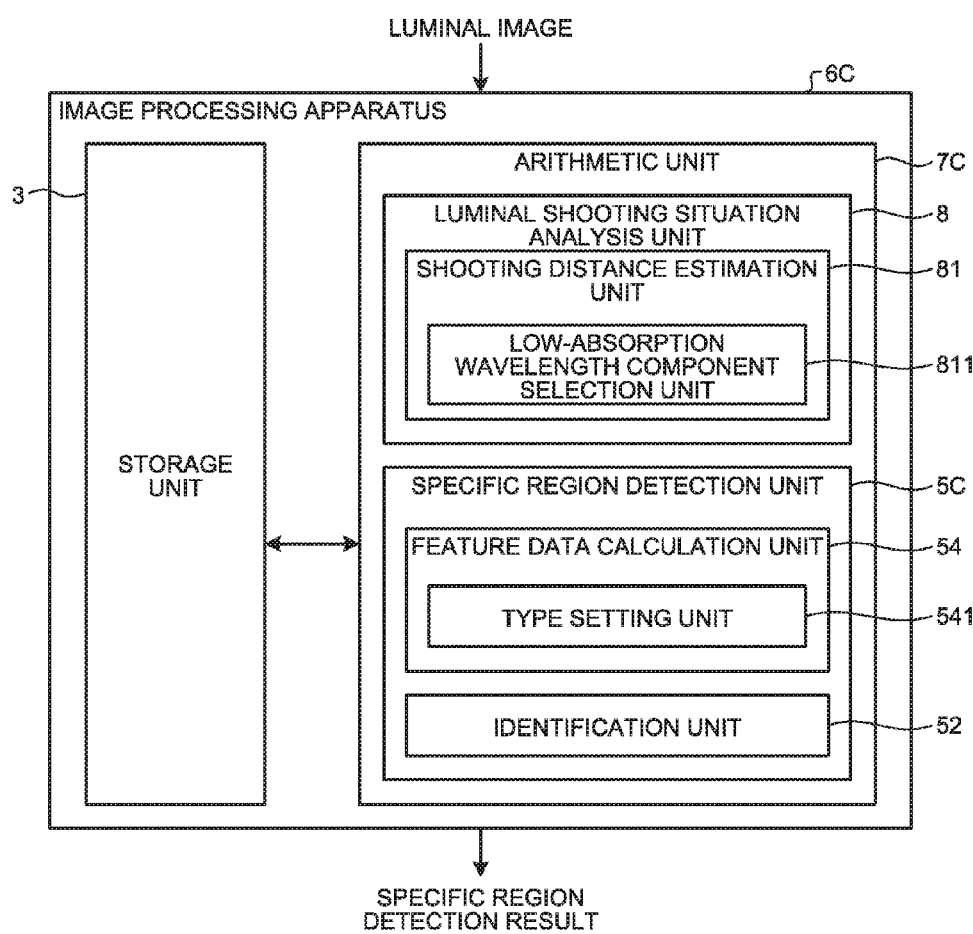
FIG. 23 is a block diagram illustrating a functional configuration of an image processing apparatus according to Modification 2-3 of the second embodiment.

FIG. 23 is a block diagram illustrating a functional configuration of an image processing apparatus according to Modification 2-3 of the second embodiment. In an image processing apparatus 6C illustrated in the same drawing, constituent parts having the same functions as those of the image processing apparatus 1C illustrated in FIG. 12 and the image processing apparatus 6 illustrated in FIG. 14 will be denoted by the same reference numerals as those in FIGS. 12 and 14.

The image processing apparatus 6C includes an arithmetic unit 7C and the storage unit 3. The arithmetic unit 7C includes the luminal shooting situation analysis unit 8 and the specific region detection unit 5C.

The specific region detection unit 5C includes the feature data calculation unit 54 and the identification unit 52. The feature data calculation unit 54 includes the type setting unit 541.

The type setting unit 541 sets a type of feature data to be used for detection of a specific region or a weight of the feature data for each type according to closeness or distantness of a shooting distance. When an average value of shooting distances calculated at a plurality of locations is smaller than a predetermined threshold, that is, when the shooting distance is close, texture and a contour line of a specific region surface are clearly reflected. In this case, the type setting unit 541 sets use of texture feature data or contour feature data among feature data of a color, a contour, a pixel value surface shape, the texture, and the like, or sets a high weight to the texture feature data or the contour feature data among the plurality of types of feature data. The type setting unit 541 performs known feature axis normalization (linear transformation such that an average becomes zero and a variance becomes one) with respect to the plurality of types of calculated feature data, and then, multiplies a coefficient such that only a variance of the texture feature data or the contour feature data becomes larger than one.

On the other hand, when the average value of the shooting distances is equal to or larger than the predetermined threshold, that is, when the shooting distance is distant, the texture becomes unclear due to a decrease in resolution, and the contour line is also likely to be unclear due to influence of dark noise or the like. In this case, however, it is possible to maintain a relatively stable state in terms of the color and the pixel value surface shape. In this case, the type setting unit 541 sets use of the color feature data or the pixel value surface shape feature data among the feature data of the color, the contour, the pixel value surface shape, the texture, and the like, or sets a higher weight to the color feature data or the pixel value surface shape feature data among the plurality of types of feature data described above than the other types of feature data.

Incidentally, when the shooting distance is close, a saturated component is likely to occur among color components. In particular, the R component is likely to be saturated in the living body. In this manner, there is a possibility that the color balance may collapse when the shooting distance is close, and thus, the type setting unit 541 may set non-use of the color feature data or may set a lower weight to the color feature data than the other types of feature data.

Figure 24:
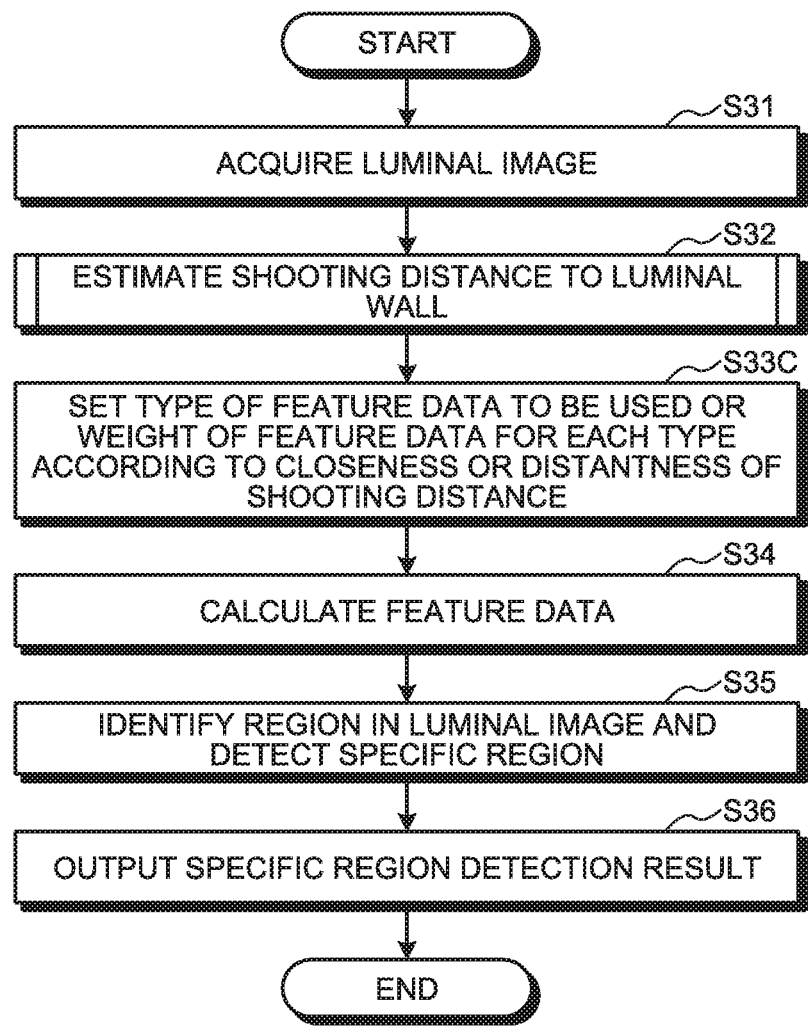
FIG. 24 is a flowchart illustrating an overview of a process performed by the image processing apparatus according to Modification 2-3 of the second embodiment.

FIG. 24 is a flowchart illustrating an overview of a process performed by the image processing apparatus 6C. In FIG. 24, the same step numbers are attached to the same processes as those of the flowchart illustrated in FIG. 15. Hereinafter, a process subsequent to Step S32 will be described.

In Step S33C, the type setting unit 541 sets the type of the feature data to be used for the specific region detection or the weight of the feature data for each type according to closeness or distantness of the shooting distance (Step S33C).

The processes of Steps S34 to S36 subsequent to Step S33C are the same as the processes that have been described in the second embodiment.

According to Modification 2-3 described above, it is possible to perform the feature data calculation, which is adaptive to a change of the feature data caused by a difference in shooting situation to put emphasis on the feature data that is clearer, and to accurately detect the specific region since the type of the feature data to be used or the weight of the feature data for each type is set in accordance with the closeness or distantness of the shooting distance.

Incidentally, the luminal shooting situation analysis unit 8A including the focus blur analysis unit 82 or the luminal shooting situation analysis unit 8B including the motion blur analysis unit 83 may be provided instead of the luminal shooting situation analysis unit 8 in Modification 2-3.

In the case of providing the luminal shooting situation analysis unit 8A, the type setting unit 541 sets the type of the feature data to be used or the weight of the feature data for each type in accordance with a degree of a focus blur. When the focus blur is small, the texture and the contour line on the specific region surface are clearly reflected. Therefore, the type setting unit 541 sets use of the texture feature data or the contour feature data among the feature data of the color, the contour, the pixel value surface shape, the texture, and the like, or sets a higher weight to the texture feature data or the contour feature data among the plurality of types of feature data described above than the other types of feature data.

On the other hand, the texture and the contour line become unclear when the degree of the focus blur is large. In this case, however, it is possible to maintain a relatively stable state in terms of the color and the pixel value surface shape. In this case, the type setting unit 541 sets use of the color feature data or the pixel value surface shape feature data among the feature data of the color, the contour, the pixel value surface shape, the texture, and the like, or sets a high weight to the color feature data or the pixel value surface shape feature data among the plurality of types of feature data described above.

In the case of providing the luminal shooting situation analysis unit 8B, the type setting unit 541 sets the type of the feature data to be used or the weight of the feature data for each type in accordance with a degree of a motion blur. When the motion blur is small, the texture and the contour line on the specific region surface are clearly reflected. In this case, the type setting unit 541 sets use of the texture feature data or the contour feature data among the feature data of the color, the contour, the pixel value surface shape, the texture, and the like, or sets a higher weight to the texture feature data or the contour feature data among the plurality of types of feature data described above than the other types of feature data.

On the other hand, the texture and the contour line become unclear when the motion blur is large. In this case, however, it is possible to maintain a relatively stable state in terms of the color and the pixel value surface shape. In this case, the type setting unit 541 sets use of the color feature data or the pixel value surface shape feature data among the feature data of the color, the contour, the pixel value surface shape, the texture, and the like, or sets a higher weight to the color feature data or the pixel value surface shape feature data among the plurality of types of feature data described above than the other types of feature data.

Incidentally, when the motion blur occurs in an endoscope of a frame sequential scheme, color shift occurs and the color feature data also becomes unstable. Accordingly, the type setting unit 541 may set non-use of the color feature data or may set a lower weight to the color feature data than the other types of feature data in this case. In addition, the feature data calculation unit 54 may be set to calculate the feature data by narrowing down to a specific color component such that the calculation of the feature data such as the contour, the pixel value surface shape, the texture, and the like is not affected by the color shift.

In Modification 2-3, the luminal shooting situation analysis unit 8 may be configured to include any two or all of the shooting distance estimation unit 81, the focus blur analysis unit 82, and the motion blur analysis unit 83.

Modification 2-4

Figure 25:
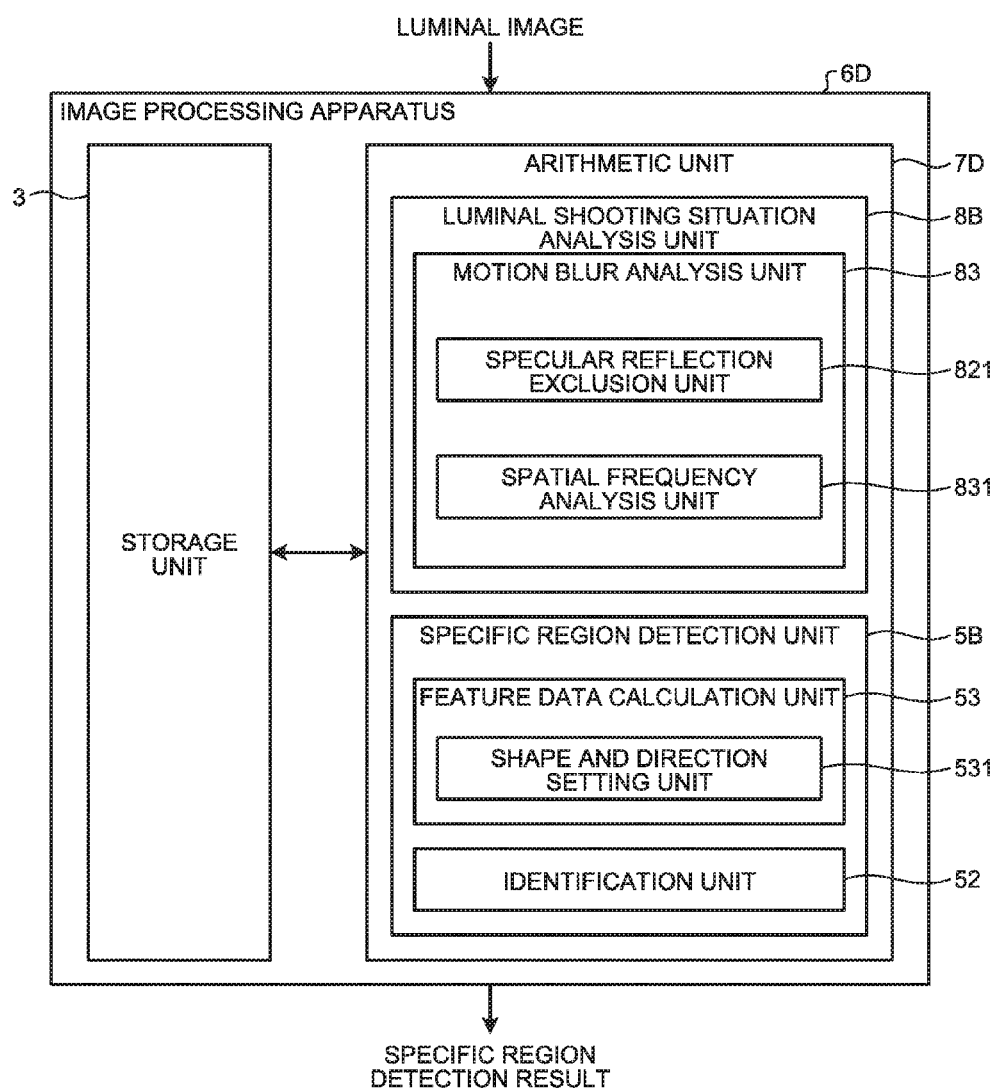
FIG. 25 is a block diagram illustrating a functional configuration of an image processing apparatus according to Modification 2-4 of the second embodiment.

FIG. 25 is a block diagram illustrating a functional configuration of an image processing apparatus according to Modification 2-4 of the second embodiment. In an image processing apparatus 6D illustrated in the same drawing, constituent parts having the same functions as those of the image processing apparatus 1B illustrated in FIG. 10 and the image processing apparatus 6 illustrated in FIG. 14 will be denoted by the same reference numerals as those in FIGS. 10 and 14.

The image processing apparatus 6D includes an arithmetic unit 7D and the storage unit 3. The arithmetic unit 7D includes the luminal shooting situation analysis unit 8B and the specific region detection unit 5B.

Figure 26:
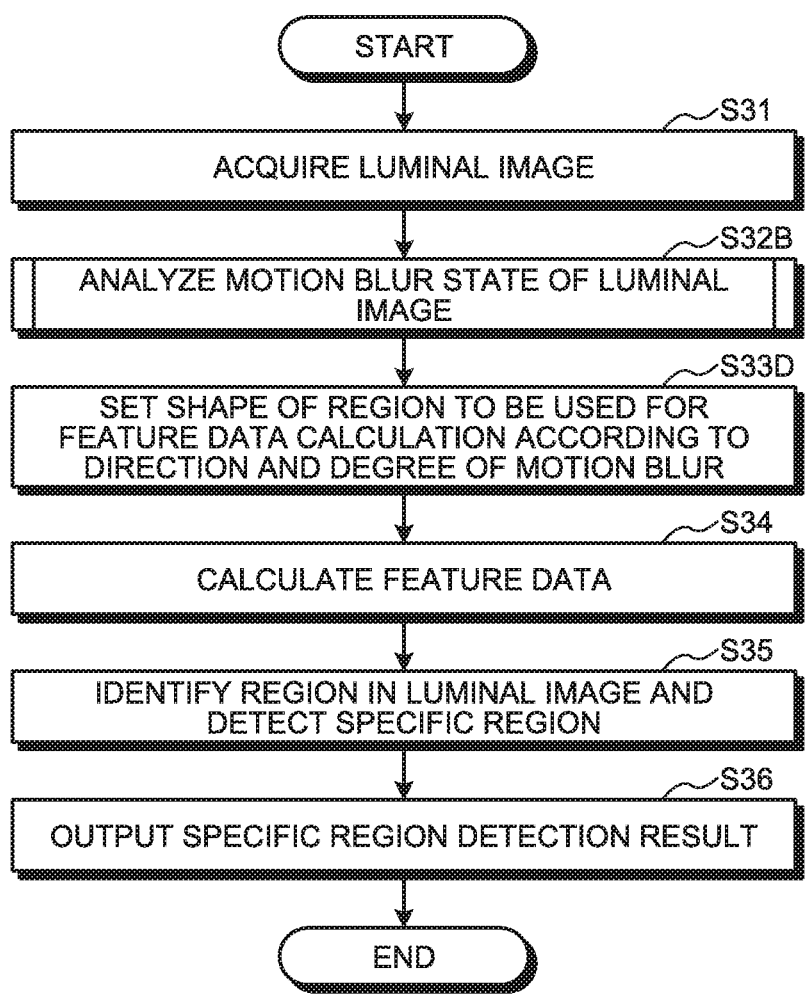
FIG. 26 is a flowchart illustrating an overview of a process performed by the image processing apparatus according to Modification 2-4 of the second embodiment.

FIG. 26 is a flowchart illustrating an overview of a process performed by the image processing apparatus 6D. In FIG. 26, the same step numbers are attached to the same processes as those of the flowchart illustrated in FIG. 21. Hereinafter, a process subsequent to Step S32B will be described.

In Step S33D, the shape and direction setting unit 531 sets a shape of a region to be used for feature data calculation in accordance with a direction and a degree of a motion blur of a luminal image (Step S33D). When the motion blur occurs in the luminal image, an object to be shot is reflected in the form of being extended in a direction of the motion blur by the degree of the motion blur. In this case, the shape and direction setting unit 531 sets a feature data calculation region having a shape of being extended in the direction of the motion blur by the degree of the motion blur. Accordingly, it is possible to sufficiently obtain information on a subject.

The processes of Steps S34 to S36 subsequent to Step S33D are the same as the processes that have been described in the second embodiment.

According to Modification 2-4 described above, it is possible to set the feature data calculation region, which is adaptive to a change of the luminal image caused by the motion blur, and to accurately detect a specific region since the shape of the region to be used for the feature data calculation is set in accordance with the degree of the motion blur.

Third Embodiment

Figure 27:
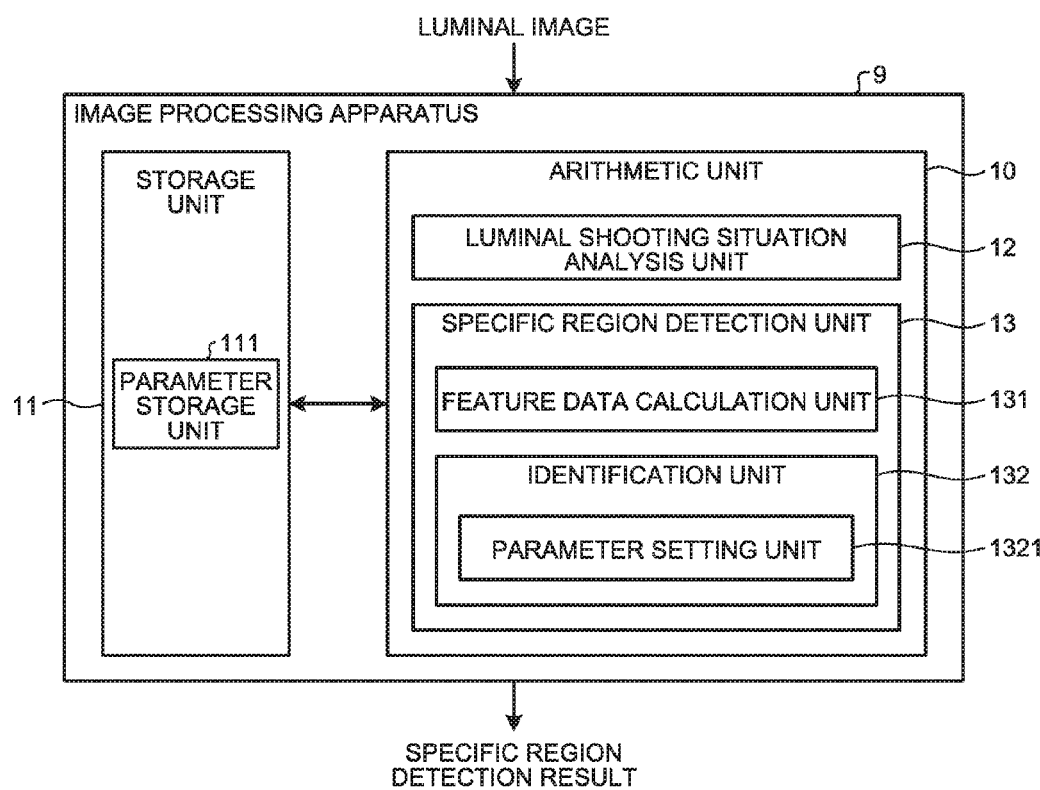
FIG. 27 is a block diagram illustrating a functional configuration of an image processing apparatus according to a third embodiment.

FIG. 27 is a block diagram illustrating a functional configuration of an image processing apparatus according to a third embodiment. In an image processing apparatus 9 illustrated in the same drawing, constituent parts having the same functions as those of the image processing apparatus 1 illustrated in FIG. 3 will be denoted by the same reference numerals as those in FIG. 3.

The image processing apparatus 9 includes an arithmetic unit 10 and a storage unit 11. The arithmetic unit 10 includes a luminal shooting situation analysis unit 12 and a specific region detection unit 13. The storage unit 11 includes a parameter storage unit 111.

The luminal shooting situation analysis unit 12 may be any one of the plurality of luminal shooting situation analysis units, which have been described in the first and second embodiments, respectively, or may be configured by appropriately combining those units.

The specific region detection unit 13 includes a feature data calculation unit 131 and an identification unit 132. The identification unit 132 includes a parameter setting unit 1321.

The parameter setting unit 1321 extracts a parameter, created based on teacher data in a luminal shooting situation equivalent to a luminal shooting situation analyzed by the luminal shooting situation analysis unit 12, from the parameter storage unit 111 of the storage unit 11, and sets the extracted parameter as a parameter of the identification unit 132. Examples of the parameter of the identification unit 132 include an identification boundary in a feature space, a distribution model in accordance with the luminal shooting situation, an identification function, a representative pattern (template), and the like. The expression, "equivalent" referred to herein means that analysis results (presence or absence and a direction of a deep portion, a magnitude and a direction of an inner wall gradient, closeness or distantness of a shooting distance, presence or absence of a focus blur, presence or absence of a motion blur, and the like) obtained by the luminal shooting situation analysis unit 12 are substantially the same while allowing a predetermined error. In practice, analysis (this analysis may be mechanical processing or manual work) similar to luminal shooting situation analysis is performed for a plurality of images obtained in advance, the respective images of analysis results are specified, and then, a parameter corresponding to each of the analysis results is created based on the teacher data in accordance with the respective analysis result images, and a parameter matching an analysis result of the luminal shooting situation of an actual processing target image is used in the identification unit 132.

For example, it is suitable to use a parameter created based on teacher data of a specific region reflected in an image obtained by obliquely shooting a luminal wall in order to detect the specific region in the image obtained by obliquely shooting the luminal wall. On the other hand, it is suitable to use a parameter created based on teacher data of a specific region reflected in an image obtained by shooting a luminal wall from the front in order to detect the specific region in the image obtained by shooting the luminal wall from the front. In regard to luminal shooting situations such as a difference of a lumen deep portion region or an inner wall gradient direction, the closeness or distantness of the shooting distance, the degree of the focus blur, and the degree of the motion blur, it is also suitable to use a parameter created based on teacher data in the equivalent luminal shooting situation. In addition, when a plurality of luminal shooting situations occurs complexly, a parameter created based on teacher data matching with such complex luminal shooting situations is most suitable.

The parameter storage unit 111 included in the storage unit 11 stores the parameters created based on the plurality of teacher data corresponding to the plurality of luminal shooting situations in association with the luminal shooting situations. Incidentally, the parameter may be stored in an external device, and the parameter setting unit 1321 may acquire the parameter from the external device and set the parameter of the identification unit 132.

Figure 28:
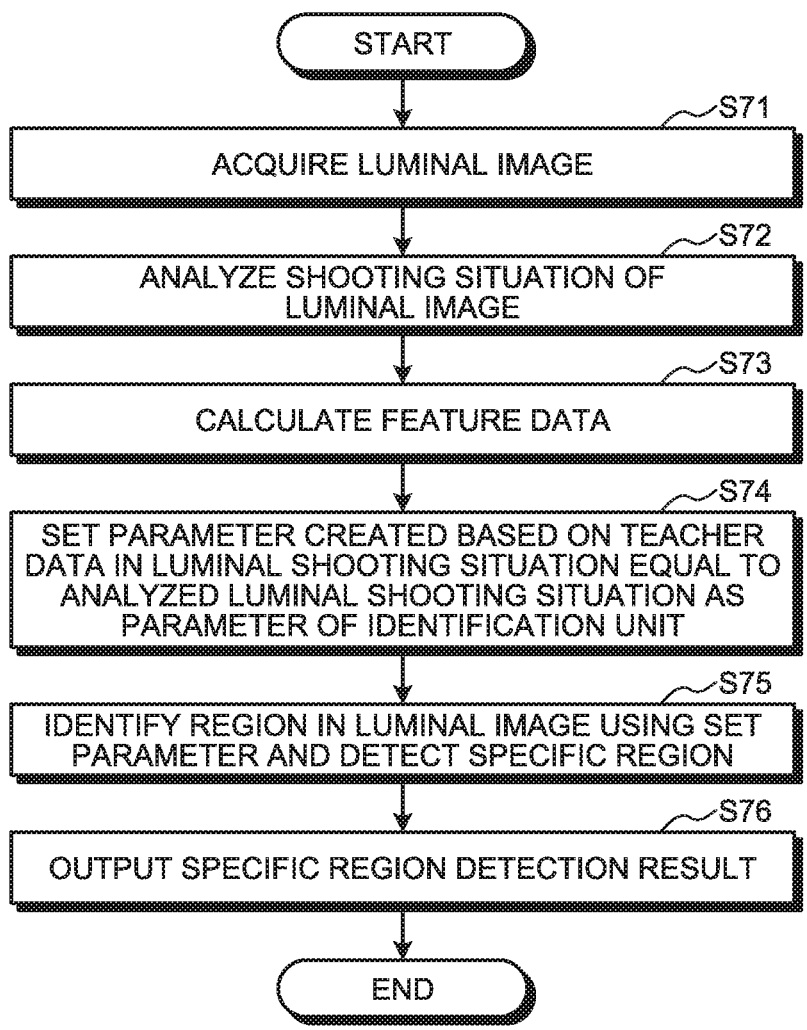
FIG. 28 is a flowchart illustrating an overview of a process performed by the image processing apparatus according to the third embodiment.

FIG. 28 is a flowchart illustrating an overview of a process executed by the image processing apparatus 9. First, the arithmetic unit 10 acquires the luminal image to be processed (Step S71).

Subsequently, the luminal shooting situation analysis unit 12 analyzes a shooting situation of the luminal image (Step S72).

Thereafter, the feature data calculation unit 131 sets a feature data calculation region at an arbitrary position in the image, and calculates feature data from within that region (Step S73). Various known items such as a color, a contour (edge), a pixel value surface shape (pixel value gradient), and texture may be considered as the feature data. A plurality of pieces of the feature data calculated are collected as a feature vector. The feature vectors corresponding to the number of feature data calculation regions that have been set are generated.

Subsequently, the parameter setting unit 1321 extracts the parameter, created based on the teacher data in the luminal shooting situation equivalent to the analyzed luminal shooting situation, from the parameter storage unit 111, and sets the extracted parameter as the parameter of the identification unit 132 (Step S74).

Thereafter, the identification unit 132 identifies a region in the luminal image using the set parameter and detects the specific region (Step S75).

Finally, the arithmetic unit 10 outputs a specific region detection result (Step S76). Accordingly, the image processing apparatus 9 ends a series of processes. Incidentally, the feature data calculation unit 131 may further perform the feature data calculation in accordance with the analysis result of the luminal shooting situation analysis unit 12 as described in the first and second embodiments.

According to the third embodiment described above, it is possible to accurately detect the specific region since the parameter of the identification unit is set in accordance with the luminal shooting situation. In addition, it is possible to accurately detect the specific region by calculating the feature data in accordance with the luminal shooting situation and setting the parameter of the identification unit 132 in accordance with the luminal shooting situation.

Fourth Embodiment

Figure 29:
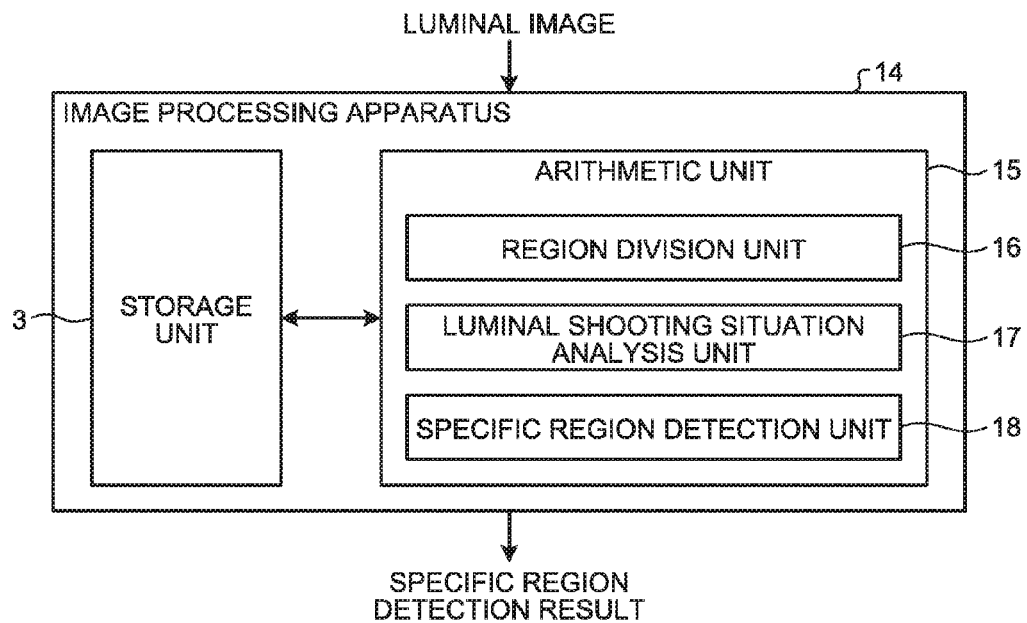
FIG. 29 is a block diagram illustrating a functional configuration of an image processing apparatus according to a fourth embodiment.

FIG. 29 is a block diagram illustrating a functional configuration of an image processing apparatus according to a fourth embodiment. In an image processing apparatus 14 illustrated in the same drawing, constituent parts having the same functions as those of the image processing apparatus 1 illustrated in FIG. 3 will be denoted by the same reference numerals as those in FIG. 3.

The image processing apparatus 14 includes an arithmetic unit 15 and the storage unit 3. The arithmetic unit 15 includes a region division unit 16, a luminal shooting situation analysis unit 17, and a specific region detection unit 18.

The region division unit 16 divides a luminal image into regions. It is possible to exemplify methods such as division in to a predetermined size of rectangles, and region division based on edges (see JP 2012-238041 A) may be exemplified as a method of region division.

Incidentally, the division may be performed such that rectangles partially overlap each other in the case of performing the rectangle division.

The luminal shooting situation analysis unit 17 may be any one of the plurality of luminal shooting situation analysis units, which have been described in the first and second embodiments, respectively, or may be one obtained by appropriately combining those units.

The specific region detection unit 18 may be any one of the plurality of specific region detection units, which have been described in the first to third embodiments, respectively, or may be one obtained by appropriately combining those units.

Figure 30:
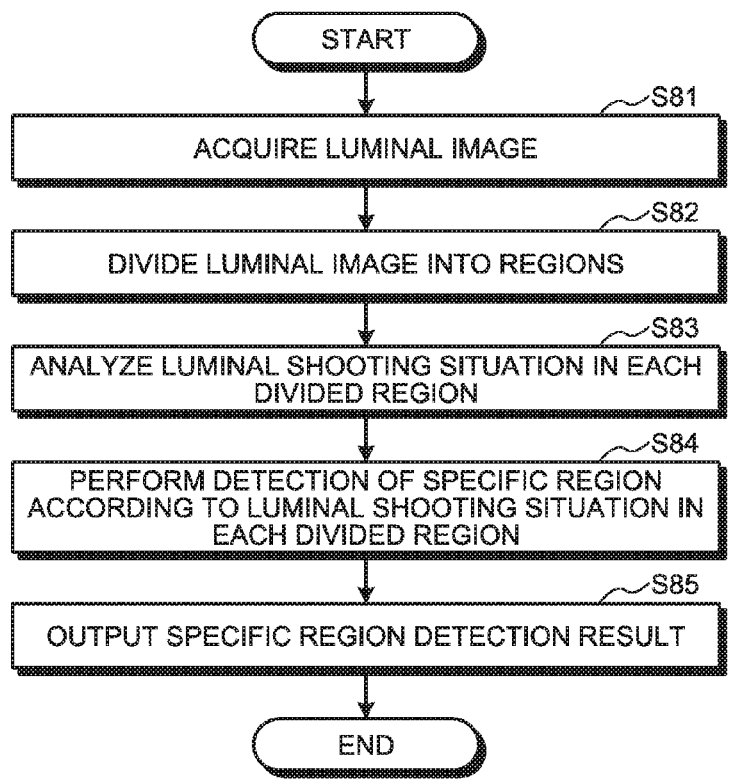
FIG. 30 is a flowchart illustrating an overview of a process performed by the image processing apparatus according to the fourth embodiment.

FIG. 30 is a flowchart illustrating an overview of a process executed by the image processing apparatus 14. First, the arithmetic unit 15 acquires the luminal image to be processed (Step S81).

Subsequently, the region division unit 16 divides the luminal image into regions (Step S82).

Thereafter, the luminal shooting situation analysis unit 17 analyzes the luminal shooting situation in each divided region (Step S83).

Subsequently, the specific region detection unit 18 detects the specific region in accordance with the luminal shooting situation for each divided region (Step S84).

Finally, the arithmetic unit 15 outputs a specific region detection result (Step S85). Accordingly, the image processing apparatus 14 ends a series of processes.

According to the fourth embodiment described above, it is possible to accurately detect the specific region since the specific region detection in accordance with the luminal shooting situation is performed for each divided region.

Other Embodiments

The modes for carrying out the present disclosure have been described hereinbefore. However, the present disclosure is not limited only to the first to fourth embodiments described above. For example, the present disclosure may be applied to luminal images of virtual endoscopes generated in CT colonography and luminal images shot by industrial endoscopes in addition to images of endoscopes for a living body.

As described above, the present disclosure may include various embodiments and the like that are not described herein.

According to the present disclosure, the specific region is detected in accordance with a shooting situation inside the lumen, it is possible to accurately detect the specific region inside the lumen.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
a processor comprising hardware, wherein the processor is configured to:
analyze a luminal shooting situation determined based on a relationship between a subject and an image sensor that shoots the subject in a luminal image obtained by shooting an inside of a lumen;
set a calculation range in the luminal image depending on the luminal shooting situation, the calculation range being a range where feature data of the luminal image is calculated;
calculate the feature data of the luminal image within the calculation range; and
detect, from the luminal image, a specific region that satisfies a specific condition based on the feature data.

2. The image processing apparatus according to claim 1, wherein the processor is configured to:
perform at least one of:
detect a lumen deep portion region in the luminal image; and
calculate magnitude of a gradient of a luminal wall in the luminal image; and
vary a size of the calculation range based on at least one of presence or absence of the lumen deep portion region and the magnitude of the gradient of the luminal wall.

3. The image processing apparatus according to claim 2, wherein the processor is configured to set the calculation range for a case where the lumen deep portion region is not present to be smaller than the calculation range for a case where the lumen deep portion region is present.

4. The image processing apparatus according to claim 2, wherein the processor is configured to set the calculation range for a case where the magnitude of the gradient of the luminal wall is smaller than a threshold to be smaller than the calculation range for a case where the gradient of the luminal wall is equal to or larger than the threshold.

5. The image processing apparatus according to claim 1, wherein the processor is configured to:
perform at least one of:
estimate a shooting distance to a luminal wall in the luminal image;
analyze a state of a focus blur of the luminal image; and
analyze a state of a motion blur of the luminal image; and
vary a size of the calculation range based on at least one of the shooting distance, the state of the focus blur, and the state of the motion blur.

6. The image processing apparatus according to claim 5, wherein the processor is configured to set the calculation range to be larger as the shooting distance increases, as a degree of the focus blur increases, or as a degree of the motion blur increases.

7. An image processing apparatus comprising:
a processor comprising hardware, wherein the processor is configured to:
analyze a luminal shooting situation determined based on a relationship between a subject and an image sensor that shoots the subject in a luminal image obtained by shooting an inside of a lumen; and
detect a specific region in accordance with the luminal shooting situation,
wherein the processor is configured to:
calculate feature data of the luminal image in accordance with the luminal shooting situation; and
identify a region of the luminal image based on the feature data and detect the specific region, and
wherein the processor is configured to set a shape and/or a direction of a region used for calculation of the feature data in accordance with the luminal shooting situation.

8. The image processing apparatus according to claim 7, wherein the processor is configured to:
perform at least one of:
detect a lumen deep portion region from within the luminal image; and
calculate a gradient of a luminal wall in the luminal image; and set the shape and/or the direction of the region used for calculation of the feature data based on at least one of a direction of the lumen deep portion region and a direction of the gradient of the luminal wall.

9. The image processing apparatus according to claim 8, wherein the processor is configured to set the shape of the region used for calculation of the feature data to a shape that is long with respect to the direction of the lumen deep portion region or a direction orthogonal to the direction of the gradient of the luminal wall.

10. The image processing apparatus according to claim 8, wherein the processor is configured to set the direction of the region used for calculation of the feature data by rotation and correction so as to be aligned in the direction of the lumen deep portion region or the direction of the gradient of the luminal wall.

11. The image processing apparatus according to claim 7, wherein the processor is configured to:
analyze a state of a motion blur of the luminal image; and
set the shape and/or direction of the region used for the calculation of the feature data in accordance with the state of the motion blur.

12. An image processing apparatus comprising:
a processor comprising hardware, wherein the processor is configured to:
analyze a luminal shooting situation determined based on a relationship between a subject and an image sensor that shoots the subject in a luminal image obtained by shooting an inside of a lumen; and
detect a specific region in accordance with the luminal shooting situation,
wherein the processor is configured to:
calculate feature data of the luminal image in accordance with the luminal shooting situation; and
identify a region of the luminal image based on the feature data and detect the specific region,
wherein the processor is configured to set a type of feature data to be categorized into any one of a color, a contour, a pixel value surface shape, and texture, or set a weight of feature data for each type in accordance with the luminal shooting situation,
wherein the processor is configured to:
perform at least one of:
detect a lumen deep portion region from within the luminal image; and
calculate a gradient of a luminal wall in the luminal image; and
set a type of feature data used for detection of the specific region or a weight of feature data for each type based on at least one of presence or absence of the lumen deep portion region and the gradient of the luminal wall, and
wherein the processor is configured to set contour feature data as the feature data used or set a higher weight to the contour feature data than the other types of feature data when the lumen deep portion region is present or when the gradient of the luminal wall is equal to or larger than a predetermined value.

13. An image processing apparatus comprising:
a processor comprising hardware, wherein the processor is configured to:
analyze a luminal shooting situation determined based on a relationship between a subject and an image sensor that shoots the subject in a luminal image obtained by shooting an inside of a lumen; and
detect a specific region in accordance with the luminal shooting situation,
wherein the processor is configured to:
calculate feature data of the luminal image in accordance with the luminal shooting situation; and
identify a region of the luminal image based on the feature data and detect the specific region,
wherein the processor is configured to set a type of feature data to be categorized into any one of a color, a contour, a pixel value surface shape, and texture, or set a weight of feature data for each type in accordance with the luminal shooting situation,
wherein the processor is configured to:
perform at least one of:
detect a lumen deep portion region from within the luminal image; and
calculate a gradient of a luminal wall in the luminal image; and
set a type of feature data used for detection of the specific region or a weight of feature data for each type based on at least one of presence or absence of the lumen deep portion region and the gradient of the luminal wall, and
wherein the processor is configured to set pixel value surface shape feature data or texture feature data as the feature data used or set a higher weight to the pixel value surface shape feature data or the texture feature data than the other types of feature data when the lumen deep portion region is not present or when the gradient of the luminal wall is smaller than the predetermined value.

14. An image processing apparatus comprising:
a processor comprising hardware, wherein the processor is configured to:
analyze a luminal shooting situation determined based on a relationship between a subject and an image sensor that shoots the subject in a luminal image obtained by shooting an inside of a lumen; and
detect a specific region in accordance with the luminal shooting situation,
wherein the processor is configured to:
calculate feature data of the luminal image in accordance with the luminal shooting situation; and
identify a region of the luminal image based on the feature data and detect the specific region,
wherein the processor is configured to set a type of feature data to be categorized into any one of a color, a contour, a pixel value surface shape, and texture, or set a weight of feature data for each type in accordance with the luminal shooting situation,
wherein the processor is configured to:
perform at least one of:
estimate a shooting distance to a luminal wall in the luminal image;
analyze a state of a focus blur of the luminal image; and
analyze a state of a motion blur of the luminal image; and
set a type of feature data used for detection of the specific region or a weight of feature data for each type based on at least one of the shooting distance, the state of focus blur, and the state of motion blur, and
wherein the processor is configured to set color feature data or pixel value surface shape feature data as the feature data used or set a higher weight to the color feature data or the pixel value surface shape feature data than the other types of feature data when the shooting distance is large, when a degree of the focus blur is equal to or larger than a predetermined degree, or when a degree of the motion blur is equal to or larger than a predetermined degree.

15. An image processing apparatus comprising:
a processor comprising hardware, wherein the processor is configured to:
   analyze a luminal shooting situation determined based on a relationship between a subject and an image sensor that shoots the subject in a luminal image obtained by shooting an inside of a lumen; and
   detect a specific region in accordance with the luminal shooting situation,
wherein the processor is configured to:
   calculate feature data of the luminal image in accordance with the luminal shooting situation; and
   identify a region of the luminal image based on the feature data and detect the specific region,
wherein the processor is configured to set a type of feature data to be categorized into any one of a color, a contour, a pixel value surface shape, and texture, or set a weight of feature data for each type in accordance with the luminal shooting situation,
wherein the processor is configured to:
   perform at least one of:
      estimate a shooting distance to a luminal wall in the luminal image;
      analyze a state of a focus blur of the luminal image; and
      analyze a state of a motion blur of the luminal image; and
   set a type of feature data used for detection of the specific region or a weight of feature data for each type based on at least one of the shooting distance, the state of focus blur, and the state of motion blur, and wherein the processor is configured to set texture feature data or contour feature data as the feature data used or set a higher weight to the texture feature data or the contour feature data than the other types of feature data when the shooting distance is small, when the degree of the focus blur is smaller than the predetermined degree, or when the degree of the motion blur is smaller than the predetermined degree.

16. An image processing method comprising:
analyzing a luminal shooting situation determined based on a relationship between a subject and an image sensor that shoots the subject in a luminal image obtained by shooting an inside of a lumen;
setting a calculating range in the luminal image depending on the luminal shooting situation, the calculation range being a range where feature data of the luminal image is calculated;
calculating the feature data of the luminal image within the calculation range; and
detecting, from the luminal image, a specific region that satisfies a specific condition based on the feature data.

17. A non-transitory computer-readable recording medium with an executable program stored thereon, the program causing a processor to execute:
analyzing a luminal shooting situation determined based on a relationship between a subject and an image sensor that shoots the subject in a luminal image obtained by shooting an inside of a lumen;
setting a calculation range in the luminal image depending on the luminal shooting situation, the calculation range being a range where feature data of the luminal image is calculated;
calculating the feature data of the luminal image within the calculation range; and
detecting, from the luminal image, a specific region that satisfies a specific condition based on the feature data.

* * * * *